(12) United States Patent
Burke et al.

(10) Patent No.: US 12,090,164 B2
(45) Date of Patent: Sep. 17, 2024

(54) GENOTYPE-AGNOSTIC RESCUE OF CYSTIC FIBROSIS WITH SMALL MOLECULE BICARBONATE CHANNELS

(71) Applicants: The Board of Trustees of the University of Illinois, Urbana, IL (US); University of Iowa Research Foundation, Iowa City, IA (US)

(72) Inventors: Martin D. Burke, Champaign, IL (US); Katrina A. Muraglia, Champaign, IL (US); Rajeev S. Chorghade, Champaign, IL (US); Michael J. Welsh, Iowa City, IA (US)

(73) Assignees: The Board of Trustees of the University of Illinois, Urbana, IL (US); University of Iowa Research Foundation, Iowa City, IA (US)

( * ) Notice: Subject to any disclaimer, the term of this patent is extended or adjusted under 35 U.S.C. 154(b) by 20 days.

(21) Appl. No.: 16/754,651

(22) PCT Filed: Oct. 11, 2018

(86) PCT No.: PCT/US2018/055435
§ 371 (c)(1),
(2) Date: Apr. 8, 2020

(87) PCT Pub. No.: WO2019/075214
PCT Pub. Date: Apr. 18, 2019

(65) Prior Publication Data
US 2020/0352970 A1    Nov. 12, 2020

Related U.S. Application Data

(60) Provisional application No. 62/570,795, filed on Oct. 11, 2017.

(51) Int. Cl.
*A61K 31/7048* (2006.01)
*A61K 9/00* (2006.01)
(Continued)

(52) U.S. Cl.
CPC ......... *A61K 31/7048* (2013.01); *A61K 9/008* (2013.01); *A61K 9/127* (2013.01); *A61K 31/575* (2013.01); *A61P 11/00* (2018.01)

(58) Field of Classification Search
None
See application file for complete search history.

(56) References Cited

U.S. PATENT DOCUMENTS

| 7,544,369 B2* | 6/2009 | Boni .................... A61K 31/407 |
| | | 424/450 |
| 10,960,018 B2* | 3/2021 | Rowe ................. A61K 31/4184 |

(Continued)

FOREIGN PATENT DOCUMENTS

| EP | 3439668 A1 | 2/2019 |
| JP | H01160915 A | 6/1989 |

(Continued)

OTHER PUBLICATIONS

Adler-Moore et al (Medical Mycology, 2016, 54(3), 223-231). (Year: 2016).*

(Continued)

*Primary Examiner* — Celeste A Roney
(74) *Attorney, Agent, or Firm* — Foley Hoag LLP; Dana M. Gordon; Benjamin A. Vaughan

(57) ABSTRACT

Disclosed are methods of treating cystic fibrosis using AmB and a sterol or compositions comprising AmB and a sterol. Also disclosed are methods of increasing the pH of airway surface liquid in a patient having cystic fibrosis using AmB (Continued)

and a sterol; and methods of decreasing the viscosity of airway surface liquid in a patient having cystic fibrosis using AmB and a sterol.

20 Claims, 15 Drawing Sheets

(51) Int. Cl.
*A61K 9/127* (2006.01)
*A61K 31/575* (2006.01)
*A61P 11/00* (2006.01)

(56) References Cited

U.S. PATENT DOCUMENTS

| | | |
|---|---|---|
| 2005/0129767 A1 | 6/2005 | Tsai et al. |
| 2014/0109899 A1 | 4/2014 | Boucher et al. |
| 2014/0194365 A1 | 7/2014 | Feghali-Bostwick et al. |
| 2020/0352970 A1 | 11/2020 | Burke et al. |

FOREIGN PATENT DOCUMENTS

| | | | | |
|---|---|---|---|---|
| JP | 2008/501782 A | 1/2008 | | |
| JP | 7041961 B2 | 3/2022 | | |
| WO | WO-2016073462 A1 * | 5/2016 | ......... | A61K 31/7048 |
| WO | WO-2017177228 A1 * | 10/2017 | ......... | A61K 31/7048 |
| WO | WO-2019/075214 A2 | 4/2019 | | |

OTHER PUBLICATIONS

Veit et al (Sci Transl Med, 2014, 6(246)). (Year: 2014).*
De Amorim et al (University of Lisbon, Dissertation) (Year: 2013).*
Gilead Sciences, "AmBisome (Amphotericin B) Liposome for injection," downloaded from the internet <https://www.gilead.com/~/media/files/pdfs/medicines/other/ambisome_pi.pdf?la=en>. (2018).
International Search Report and Written Opinion for International Application No. PCT/US2018/055435 dated Dec. 26, 2018.
Proesmans et al., "Use of nebulized amphotericin B in the treatment of allergic bronchopulmonary aspergillosis in cystic fibrosis," International Journal of Pediatrics, 2010:1-9 (2010).
Extended European Search Report for EP Application No. EP 18865483 mailed May 12, 2021.
Siempos et al., "Nebulised corticosteroid and amphotericin B: an alternative treatment for ABPA?," European Respiratory Journal, 31(4): 908-909 (2008).
Casciaro et al., "Role of nebulized amphotericin B in the management of allergic bronchopulmonary aspergillosis in cystic fibrosis: Case report and review of literature," Journal of Chemotherapy, 27(5): 307-311 (2015).
De Boeck et al., "Progress in therapies for cystic fibrosis," Lancet Respir Med 4: pp. 662-674 (2016).
Stanke et al., "Classification of CFTR mutation classes," Lancet Respir Med 4: 1 page (2016).
Tiddens et al., "Inhaled antibiotics: dry or wet?," European Respiratory Journal, 44: 1308-1318 (2014).
De Amorim et al., "Characterization of CFTR nonsense mutations using novel CTFR minigenes" (University of Lisbon, Dissertation) (Year: 2013).

* cited by examiner

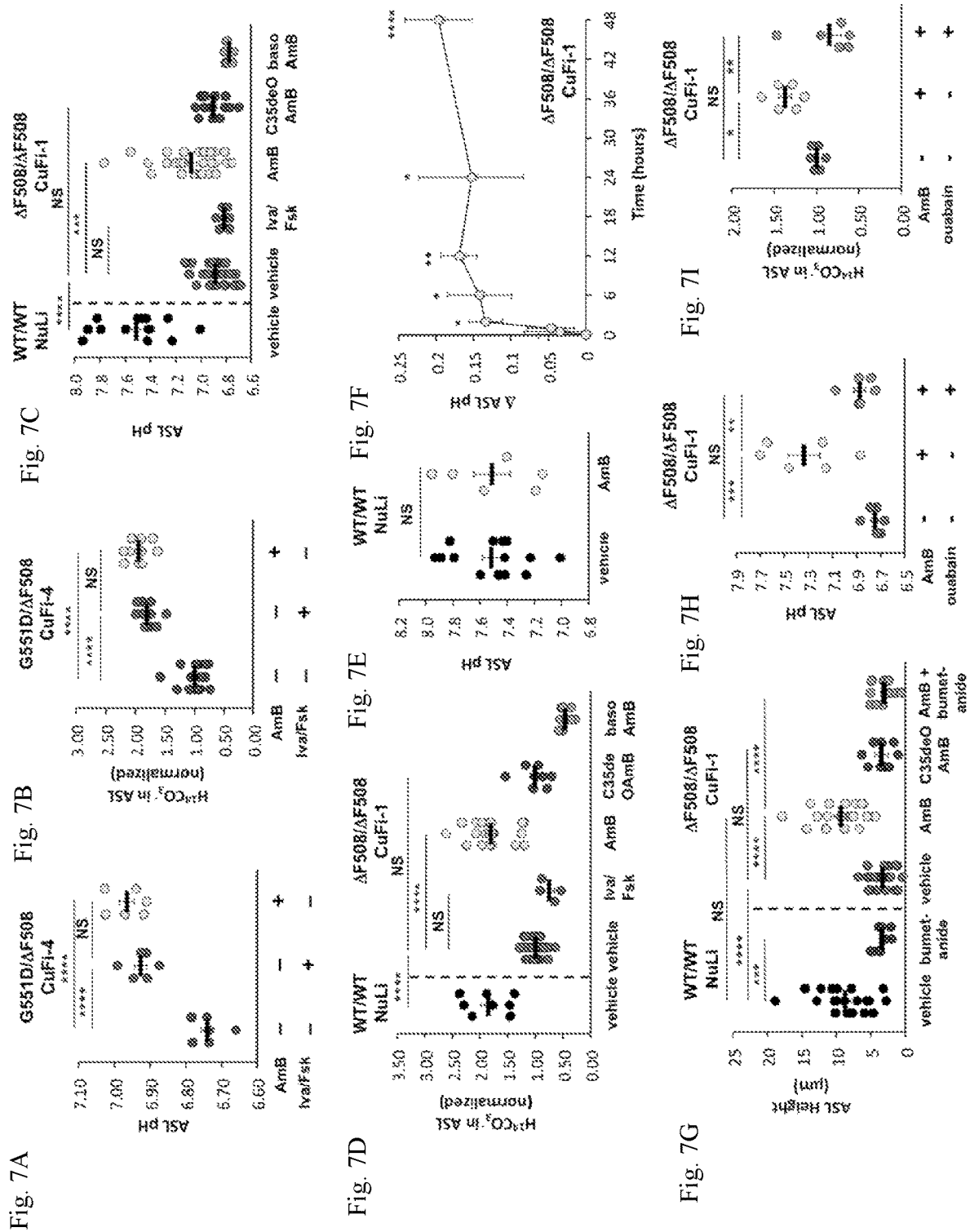

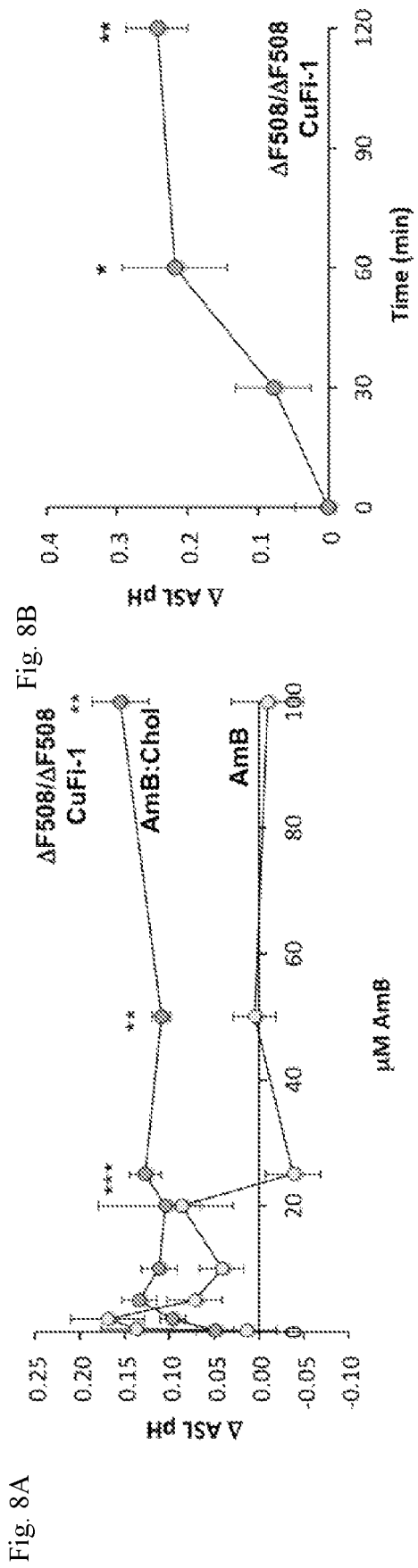
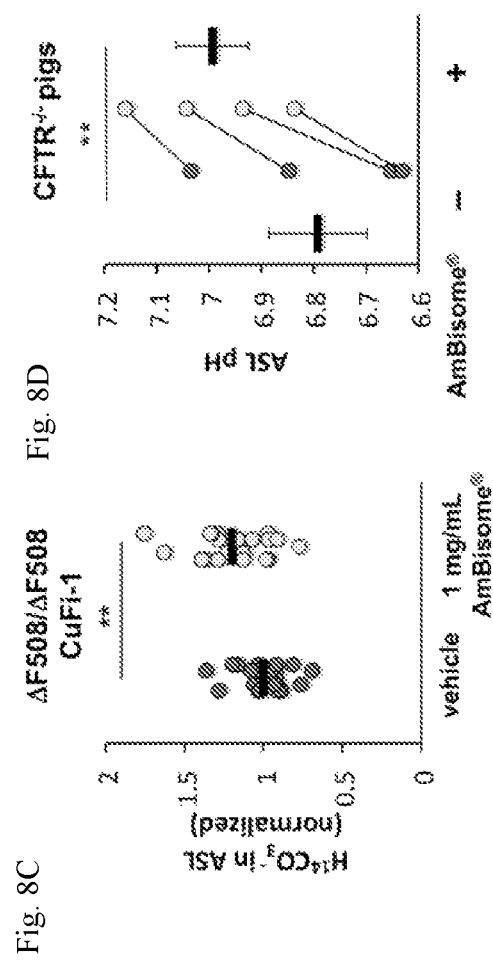
Fig. 8A  Fig. 8B  Fig. 8C  Fig. 8D

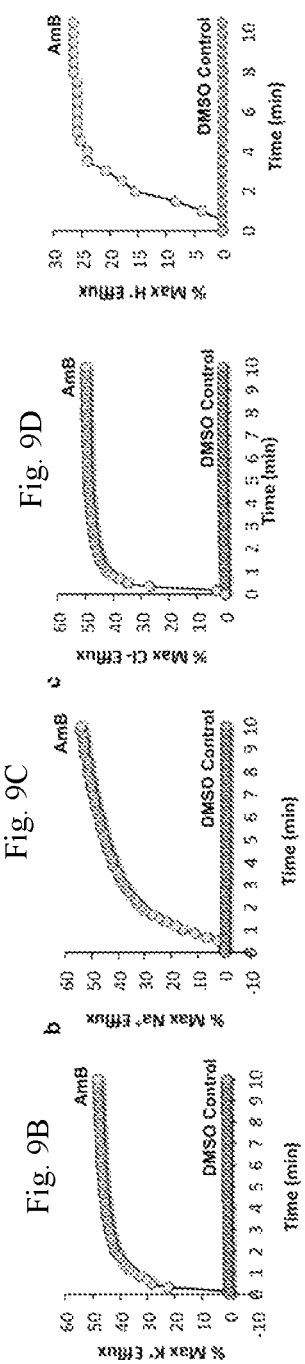
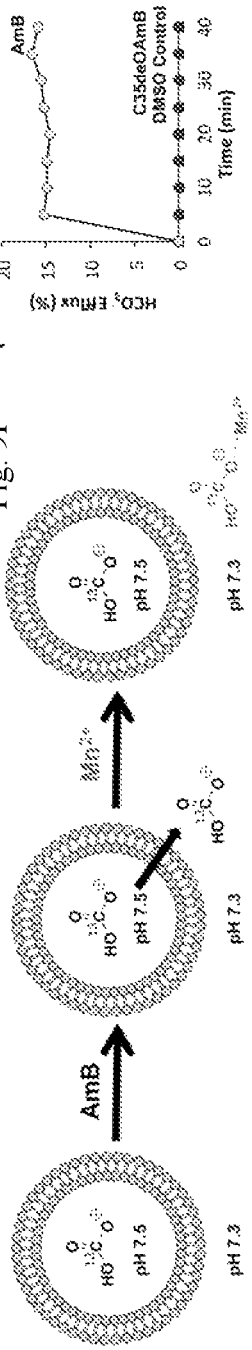
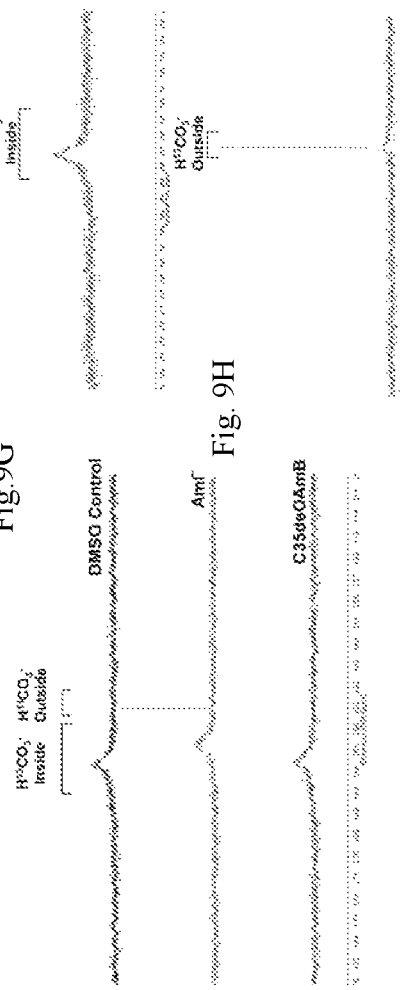
Fig. 9A Fig. 9B Fig. 9C Fig. 9D Fig. 9E Fig. 9F Fig. 9G Fig. 9H Fig. 9I

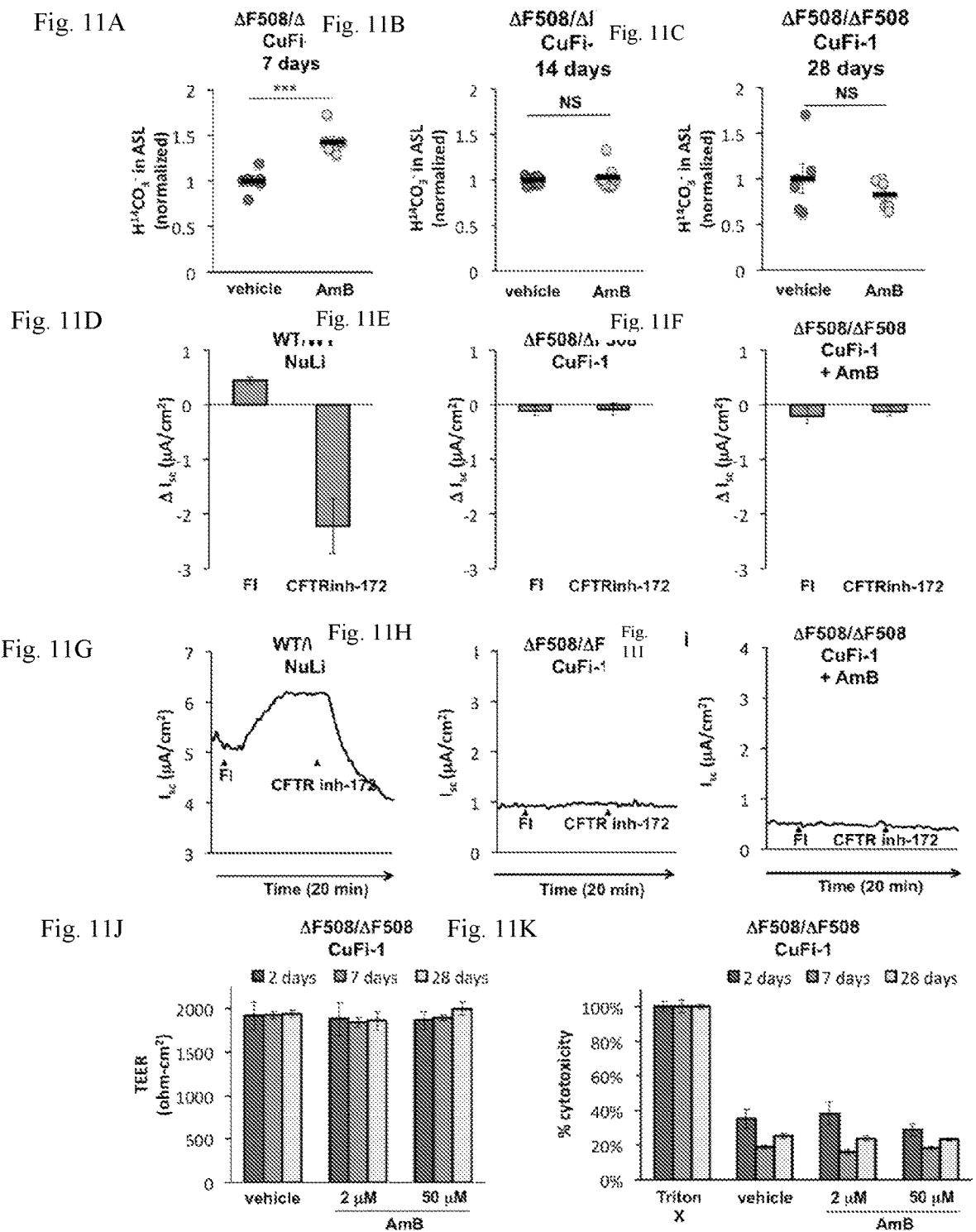

scale bar = 10 microns

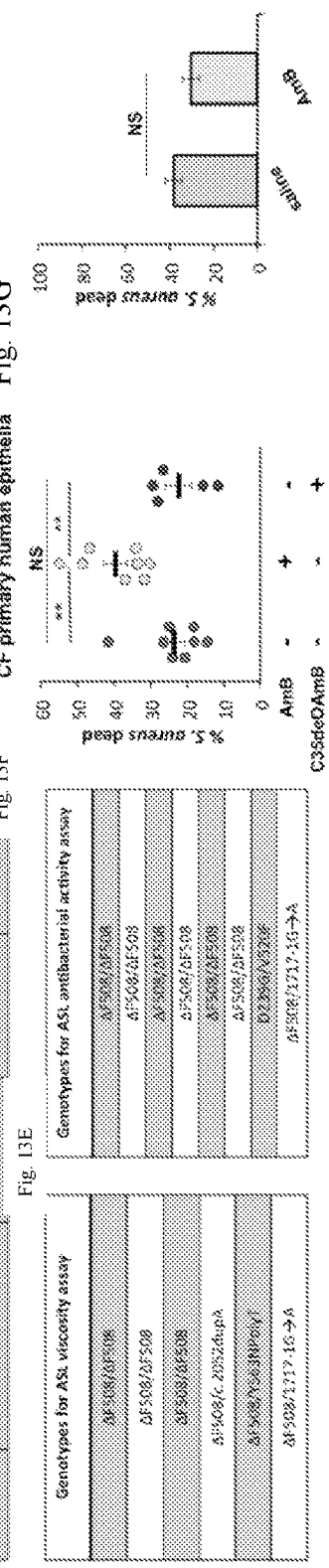

GENOTYPE-AGNOSTIC RESCUE OF CYSTIC FIBROSIS WITH SMALL MOLECULE BICARBONATE CHANNELS

RELATED APPLICATIONS

This application is the National Stage of International Patent Application No. PCT/US2018/055435, filed Oct. 11, 2018, which claims the benefit of priority to U.S. Provisional Patent Application Ser. No. 62/570,795, filed Oct. 11, 2017.

GOVERNMENT SUPPORT

This invention was made with government support under grant number GM118185, awarded by The National Institutes of Health. The government has certain rights in the invention.

BACKGROUND OF THE INVENTION

Cystic fibrosis is an autosomal recessive genetic disease that substantially shortens lifespan in affected individuals. It occurs in 1 in 3,000 live births, and is caused by mutations in the CFTR gene encoding cystic fibrosis transmembrane conductance regulator (CFTR), a membrane-expressed anion channel protein in vertebrates. The disease is most often characterized by chronic and potentially fatal respiratory infections, and for most patients with cystic fibrosis, only symptomatic treatments are available. The median survival of patients is only 33 years.

CFTR is an ABC transporter-class ion channel that conducts chloride and bicarbonate ions across epithelial cell membranes. Mutations of the CFTR gene affecting chloride and bicarbonate ion channel function lead to dysregulation of airway surface liquid (ASL) pH and epithelial fluid transport in the lung, pancreas and other organs, resulting in cystic fibrosis. Complications include decreased ASL pH, increased ASL viscosity, decreased ASL antibacterial activity, thickened mucus in the lungs with frequent respiratory infections, and pancreatic insufficiency giving rise to malnutrition and diabetes. These conditions lead to chronic disability and reduced life expectancy. In male patients the progressive obstruction and destruction of the developing vas deferens and epididymis appear to result from abnormal intraluminal secretions, causing congenital absence of the vas deferens and male infertility.

CFTR functions as a cAMP-activated ATP-gated anion channel, increasing the conductance for certain anions (e.g., Cl$^-$ and bicarbonate) to flow down their electrochemical gradient. ATP-driven conformational changes in CFTR open and close a gate to allow transmembrane flow of anions down their electrochemical gradient. This function is in contrast to other ABC proteins, in which ATP-driven conformational changes fuel uphill substrate transport across cellular membranes. Essentially, CFTR is an ion channel that evolved as a "broken" ABC transporter that leaks when in the open conformation.

Mutations of the CFTR gene affecting anion channel function lead to dysregulation of epithelial ion and fluid transport, thickened mucus, and frequent respiratory infections in the lung, primarily causing the life-shortening pathophysiology associated with cystic fibrosis. CFTR is found in the epithelial cells of many organs including the lung, liver, pancreas, digestive tract, reproductive tract, and skin. In the lung, the protein ion channel moves bicarbonate and chloride ions out of an epithelial cell to the apical airway surface liquid (ASL). This maintains proper ASL pH, viscosity, and activity of pH-sensitive antimicrobial proteins. Changes in the ASL due to CFTR dysfunction impair the clearance and killing of bacteria, leaving patients vulnerable to the chronic airway infections that are the primary driver of morbidity and mortality.

Almost 2000 CFTR mutations are found in CF patients, hundreds of which are confirmed to cause disease through at least five different mechanisms of functional loss (1). Genotype-specific small molecule drugs can increase the activity of certain mutant forms of CFTR. However, most CF patients have mutations that are either non-responsive or minimally-responsive to currently available treatments (2). Extensive efforts to develop gene therapy for CF have yet to yield substantial clinical impact (1). Thus, a compelling need exists for effective treatments of cystic fibrosis that are agnostic to the genotype of the CTFR mutation.

Restoring anion secretion through CFTR channels that bear specific mutations improves airway host defenses and lung function in people with CF (1, 27, 38). However, not all CFTR mutations are amenable to medicines that target the defective protein (39). A small molecule ion channel that promotes secretion of anions can circumvent these limitations. Multiple studies have demonstrated that peptide or small molecule ion channels, transporters, or carriers can promote chloride transport in CFTR-deficient cells and/or changes in short circuit current or potential in CFTR-deficient epithelia (37, 11-13, 40). However, it has remained unclear whether this approach can restore airway host defenses.

SUMMARY OF THE INVENTION

In certain aspects, the present invention provides methods of treating cystic fibrosis, comprising conjointly administering to a patient in need thereof a therapeutically effective amount of (i) amphotericin B (AmB) or a pharmaceutically acceptable salt or hydrate thereof, and (ii) a sterol or a pharmaceutically acceptable salt thereof, thereby treating the cystic fibrosis.

Also provided herein are methods of increasing the pH of airway surface liquid in a patient having cystic fibrosis, comprising administering to a patient having cystic fibrosis a therapeutically effective amount of (i) amphotericin B (AmB) or a pharmaceutically acceptable salt or hydrate thereof, and (ii) a sterol or a pharmaceutically acceptable salt thereof, thereby increasing the pH of airway surface liquid in the patient having cystic fibrosis.

Further provided herein are methods of decreasing the viscosity of airway surface liquid in a patient having cystic fibrosis, comprising administering to a patient having cystic fibrosis a therapeutically effective amount of (i) amphotericin B (AmB) or a pharmaceutically acceptable salt or hydrate thereof, and (ii) a sterol or a pharmaceutically acceptable salt thereof, thereby decreasing the viscosity of airway surface liquid in the patient having cystic fibrosis.

Further provided herein are methods of increasing the antimicrobial activity of airway surface liquid in a patient having cystic fibrosis, comprising administering to a patient having cystic fibrosis a therapeutically effective amount of (i) amphotericin B (AmB) or a pharmaceutically acceptable salt or hydrate thereof, and (ii) a sterol or a pharmaceutically acceptable salt thereof, thereby increasing the antimicrobial activity of airway surface liquid in the patient having cystic fibrosis.

In certain embodiments of the methods provided herein, the conjoint administration of AmB and the sterol is accomplished via the administration of the drug product AmBisome® (i.e., a composition consisting essentially of water, AmB, and a liposomal membrane consisting of hydrogenated soy phosphatidylcholine, cholesterol, distearoylphosphatidylglycerol, alpha tocopherol, sucrose, and disodium succinate hexahydrate).

BRIEF DESCRIPTION OF THE DRAWINGS

FIGS. 7A-7I generally show that AmB increased $H^{14}CO_3^{31}$ secretion and ASL pH in cultured CF airway epithelia. Panels A-I show the effects of ivacaftor/forskolin (10 μM, 2 hours) and apical AmB (2 μM; 48 hours). FIG. 7A is a chart showing ASL pH in CuFi-4 (G551D/ΔF508) epithelia (n=10 to 16). FIG. 7B is a chart showing the rate of basolateral to apical $H^{14}CO_3^-$ secretion over 10 minutes normalized to vehicle-treated CuFi-4 epithelia (n=10 to 16). FIG. 7C is a chart showing ASL pH in NuLi (CFTR$^{+/+}$) epithelia or in CuFi-1 (ΔF508/ΔF508) epithelia 48 h after addition of vehicle (FC-72), ivacaftor/forskolin (10 μM; 2 hours), C35deOAmB (2 μM; 48 hours), or basolateral addition of AmB (2 μM; 48 hours) (n=6 to 14). FIG. 7D is a chart showing the rate of $H^{14}CO_3^-$ secretion over 10 minutes in NuLi epithelia or in CuFi-1 epithelia after apical addition of vehicle (FC-72), ivacaftor/forskolin (10 μM, 2 hours), AmB (2 μM, 48 hours), C35deOAmB (2 μM; 48 hours), or basolateral addition of AmB (2 μM; 48 hours) (n=4 to 38). Values are normalized to vehicle-treated CuFi-1 epithelia. FIG. 7E is a chart that shows the effect of AmB (2 μM; 48 hours) on ASL pH in NuLi (CFTR$^{+/+}$) epithelia (n=6 to 14). FIG. 7F is a chart showing the difference in ASL pH in CuFi-1 epithelia with or without apical addition of AmB (2 μM) as a function of time (n=6 to 28). FIG. 7G is a chart showing ASL height, as quantified by confocal microscopy, in NuLi (CFTR$^{+/+}$) epithelia or in CuFi-1 epithelia after apical addition of AmB or C35deOAmB (0.5 µM; 48 hours) or basolateral addition of bumetanide (500 µM) (n=6 to 21). FIG. 7H is a chart showing ASL pH and H$^{14}$CO$_3^-$ secretion. FIG. 7I is a chart that shows CuFi-1 epithelia after addition of vehicle (FC-72), apical addition of AmB (2 µM; 48 hours), or apical addition of AmB (2 µM, 48 hours) and basolateral addition of ouabain (10 mM) (n=6). All compounds were administered in FC-72. In all Figures, measurements were taken from distinct samples and graphs depict means SEM. Two-sided unpaired Student's t tests with or without Welch's correction and ANOVA were used where appropriate to assess statistical significance; in panel 2d, * indicate statistical differences as compared to vehicle control; NS, not significant; *P≤0.05; P≤0.01; *P≤0.001; ****P≤0.0001.

FIGS. 8A-8D generally show that AmBisome® increased ASL pH in cultured CF airway epithelia and in CFTR$^{-/-}$ pigs. FIG. 8A is a chart showing the concentration-dependent effect of AmB or a pre-formed AmB:cholesterol complex on ASL pH in CuFi-1 (ΔF508/ΔF508) epithelia (n=9 to 31). FIG. 8B is a chart showing the effect of AmBisome® (1 mg/mL in FC-72) on ASL pH in CuFi-1 (ΔF508/ΔF508) as a function of time (n=9). FIG. 8C is a chart that shows H$^{14}$CO3 secretion after 2 h (n=20). FIG. 8D is a chart that shows CFTR$^{-/-}$ pigs that were treated with AmBisome® (1 mg/mL in FC-72) for at least 1 hour and ASL pH was compared to baseline (n=4). In all Figures, charts depict means SEM and two-sided unpaired Student's t tests were used to assess statistical significance; in FIG. 8A, * indicates significant differences between AmB or AmB:Chol-treated epithelia; in FIG. 8C, * indicates statistical differences as compared to vehicle control; *P≤0.05; P≤0.01; *P≤0.001. In FIG. 8A-8C measurements were taken from distinct samples. In FIG. 8D, the same pig was measured repeatedly.

FIGS. 9A-9I generally show that AmB can transport potassium, sodium, chloride, protons and HCO$_3^-$ across a lipid membrane. Traces indicate percent of maximum ion efflux after Triton-X addition. FIG. 9A is a graph showing potassium efflux from POPC/10% cholesterol liposomes in the presence of a potassium gradient after addition of [AmB] equivalent to 1:1000 AmB:lipid, or DMSO vehicle. FIG. 9B is a graph showing sodium efflux from POPC/10% cholesterol liposomes in the presence of a sodium gradient after addition of [AmB] equivalent to 1:1000 AmB:lipid, or DMSO vehicle. FIG. 9C is a graph showing chloride efflux from POPC/10% cholesterol liposomes in the presence of a chloride gradient after addition of [AmB] equivalent to 1:1000 AmB:lipid, or DMSO vehicle. FIG. 9D is a graph showing proton efflux from POPC/10% cholesterol liposomes in the presence of a pH gradient after addition of [AmB] equivalent to 1:1000 AmB:lipid, or DMSO vehicle. FIG. 9E is a schematic of the $^{13}$C-NMR experiment. FIG. 9F is a graph that shows the $^{13}$C-NMR spectra of H$^{13}$CO$_3^-$-loaded POPC/10% cholesterol liposomes treated with AmB, C35deOAmB, or DMSO vehicle. NaH$^{13}$CO$_3^-$ was loaded inside the liposomes and intravesicular solution was buffered to pH 7.5, while the extravesicular solution was buffered to pH 7.3. Due to this pH difference, intravesicular HCO$_3^-$ displays a more downfield chemical shift relative to extravesicular HCO$_3^-$. The addition of AmB (1:1,000 AmB:POPC) produces an upfield $^{13}$C signal corresponding to extravesicular HCO$_3^-$, while the addition C35deOAmB or DMSO vehicle does not, demonstrating that AmB is able to facilitate HCO$_3^-$ efflux. FIG. 9G is a spectra confirming that the upfield signal corresponds to extravesicular HCO$_3^-$, Mn$^{2+}$, which binds to HCO$_3^-$ and quenches the observed $^{13}$C signal via paramagnetic relaxation enhancement (PRE), was added to the extravesicular solution. Because Mn$^{2+}$ is impermeable to the POPC bilayer, Mn$^{2+}$ can only affect the signal corresponding to HCO$_3^-$ outside of the liposomes. The addition of Mn$^{2+}$ quenched the upfield signal produced with the addition of AmB but not the signal corresponding to intravesicular HCO$_3^-$ confirming that AmB causes efflux of HCO$_3^-$. FIG. 9H is a spectrum that shows confirmation that the broad, downfield signal corresponds to intravesicular HCO$_3^-$, POPC liposomes were lysed with Triton X at the conclusion of the experiment. FIG. 9I is a spectrum that shows a representative time course of AmB-mediated HCO$_3^-$ efflux. The data from each run was normalized to the percent of total ion release from 0 to 100%. After lysis of the liposome suspension, the integration of the signal corresponding to extravesicular HCO$_3^-$ relative to the integration of a $^{13}$C glucose standard was scaled to correspond to 100% efflux. For each experimental run with AmB addition, the signal corresponding to extravesicular HCO$_3^-$ was integrated relative to the $^{13}$C glucose standard for each FID, and the percent efflux was plotted as a function of time. In FIGS. 9A-9I, a representative spectrum or graph from at least three independent experiments is shown. In all Figures, measurements were taken from distinct samples.

FIG. 10A is a chart showing base secretion and acid absorption rates in CuFi-1 (ΔF508/ΔF508) epithelia over 20 minutes after acute addition of increasing [AmB], as measured by pH-stat titration (n=5 to 23). The apical pH was titrated to a target pH of 6.0. Student's t tests were used to assess statistical significance. FIG. 10B is a chart showing the effect of AmB (2 µM) or FC-72 vehicle after 48 hours Na$^+$ concentration in the ASL in CuFi-1 (ΔF508/ΔF508) as measured by ICP-MS (n=16). FIG. 10C is a chart showing the effect of AmB (2 µM) or FC-72 vehicle after 48 hours on K$^+$ concentration in the ASL in CuFi-1 (ΔF508/ΔF508) as measured by ICP-MS (n=16). FIG. 10D is a chart showing the effect of AmB (2 µM) or FC-72 vehicle after 48 hours on $^{24}$Mg$^{2+}$ concentrations in the ASL in CuFi-1 (ΔF508/ΔF508) as measured by ICP-MS (n=16). FIG. 10E is a chart showing the effect of AmB (2 µM) or FC-72 vehicle after 48 hours on Ca$^{2+}$ concentration in the ASL in CuFi-1 (ΔF508/ΔF508) as measured by ICP-MS (n=16). Two-sided unpaired Student's t tests with or without Welch's correction and ANOVA were used where appropriate to assess statistical significance. Graph depicts means SEM; NS, not significant; ****P≤0.0001. In all Figures, measurements were taken from distinct samples.

FIGS. 11A-11K generally show that AmB treatment is sustained, ineffective on wild type, not due to increased CFTR activity, does not disturb membrane integrity, and is non-toxic. FIG. 11A is a chart showing the effect of AmB (2 µM) or FC-72 vehicle left on the surface of CuFi-1 (ΔF508/ΔF508) epithelia for 7 days on H$^{14}$CO$_3^-$ movement from the basolateral buffer to the ASL over 10 minutes post-radiolabel addition, as normalized to FC-72 vehicle addition (n=6 to 9). FIG. 11B is a chart showing the effect of AmB (2 µM) or FC-72 vehicle left on the surface of CuFi-1 (ΔF508/ΔF508) epithelia for 14 days on H$^{14}$CO$_3^-$ movement from the basolateral buffer to the ASL over 10 minutes post-radiolabel addition, as normalized to FC-72 vehicle addition (n=6 to 9). FIG. 11C is a chart showing the effect of AmB (2 µM) or FC-72 vehicle left on the surface of CuFi-1 (ΔF508/ΔF508) epithelia for 28 days on H$^{14}$CO$_3$ movement from the basolateral buffer to the ASL over 10 minutes post-radiolabel addition, as normalized to FC-72 vehicle addition (n=6 to 9). FIGS. 11D and 11G are a graph and spectra showing changes in short-circuit current ($I_{sc}$) after treatment with 10 µM forskolin/100 µM IBMX (FI) to activate CFTR and 1 µM $CFTR_{inh}$-172 to inhibit CFTR in NuLi ($CFTR^{+/+}$) epithelia treated with AmB (2 µM; 48 hours) (n=6). FIGS. 11E and 11H are a graph and spectra showing changes in short-circuit current ($I_{sc}$) after treatment with 10 µM forskolin/100 µM IBMX (FI) to activate CFTR and 1 µM $CFTR_{inh}$-172 to inhibit CFTR in CuFi-1 (ΔF508/ΔF508) epithelia treated with AmB (2 µM; 48 hours) (n=6). FIGS. 11F and 11I are a graph and spectra showing changes in short-circuit current ($I_{sc}$) after treatment with 10 µM forskolin/100 µM IBMX (FI) to activate CFTR and 1 µM $CFTR_{inh}$-172 to inhibit CFTR in CuFi-1 epithelia treated with AmB (2 µM; 48 hours) (n=6). FIG. 11J is a chart showing that transepithelial electrical resistance (Rt) in CuFi-1 epithelia did not differ between treatment with vehicle or increasing doses of AmB over increasing time periods after a single treatment (n=9). FIG. 11K is a chart showing cytotoxicity as measured by detection of lactase dehydrogenase in CuFi-1 epithelia over increasing time periods after a single AmB or vehicle treatment, represented as percent of total cellular lysis by Triton X. AmB treatment did not cause increased cytotoxicity as compared to vehicle (n=9 to 12). In FIGS. 11A-11C, two-sided unpaired Student's t tests were used to assess statistical significance. In FIGS. 11H-11J, a representative graph from at least three independent experiments is shown. FIGS. 11A-11F, 11J, and 11K, depict means SEM; NS, not significant; ***$P \leq 0.001$ relative to vehicle control. In all Figures, measurements were taken from distinct samples.

FIG. 12A is an image showing ASL height, as imaged by confocal microscopy NuLi ($CFTR^{+/+}$) epithelia with apical addition of AmB. FIG. 12B is an image showing ASL height, as imaged by confocal microscopy, in CuFi-1 epithelia with apical addition of AmB. FIG. 12C is an image showing ASL height, as imaged by confocal microscopy, in CuFi-1 epithelia with apical addition of AmB. FIG. 12D is an image showing ASL height, as imaged by confocal microscopy, in NuLi epithelia with basolateral addition of bumetanide (500 µM). FIG. 12E is an image showing ASL height, as imaged by confocal microscopy, in AmB-treated CuFi-1 epithelia with basolateral addition of bumetanide (500 µM). Representative images from at least 8 independent experiments are shown. In all panels, measurements were taken from distinct samples. Scale bar represents 10 microns.

FIGS. 13A-13G generally show that AmB restores ASL pH and antibacterial activity in primary human airway epithelia from donors with CF. FIG. 13A is a chart showing the genotypes and A pH measurements of patient donors in an ASL pH assay. FIG. 13B is a graph showing the effects of AmB (2 µM; 48 hours), C35deOAmB (2 µM; 48 hours) and basolateral addition of AmB (2 µM; 48 hours) on the average ASL pH of primary cultured airway epithelia derived from CF humans with different CFTR mutations (n=3 to 9). FIG. 13C is a graph showing the effect of AmB (2 µM; 48 hours) on ASL pH in non-CF epithelia (n=7). FIG. 13D is a chart showing the genotypes of patient donors in an ASL viscosity assay. FIG. 13E is a chart showing the genotypes of patient donors in an ASL antibacterial activity assay. FIG. 13F is a graph showing the effect of AmB (2 µM; 48 hours) and C35deOAmB (2 µM; 48 hours) on the average ASL antibacterial activity of primary cultured airway epi- thelia derived from CF humans with a wide range of CFTR mutations (n=5 to 8). Antibacterial activity is measured by the % of *S. aureus* killed after exposure to ASL. FIG. 13G is a graph showing the ability of AmB (2 µM) alone kills *S. aureus* as compared to saline (n=36). In FIGS. 13B, 13C, 13 F and 13G, two-sided unpaired Student's t tests with or without Welch's correction and ANOVA were used where appropriate to assess statistical significance. Graphs depict means SEM; NS, not significant; *$P \leq 0.05$; **$P \leq 0.01$. In all Figures, measurements were taken from distinct samples.

FIG. 14A is a graph showing the effect of AmBisome® (1:1000 AmB:lipid ratio), AmB:Chol (1:1000 AmB:lipid ratio in DMSO), and sterile water or DMSO vehicle on $H^{13}CO_3^-$ transport across a POPC/10% cholesterol lipid membrane. FIG. 14B is a graph showing the effect of AmBisome® (1 mg/mL; 48 hours) or FC-72 vehicle on $H^{14}CO_3^-$ movement from the basolateral buffer to the ASL over 10 minutes post-radiolabel addition in CuFi-1 (ΔF508/ΔF508) as normalized to FC-72 vehicle addition (n=16). FIG. 14C is a graph showing the effect of increasing AmBisome® (1 mg/mL; 48 hours) on ASL pH in CuFi-1 epithelia as compared to vehicle control (n=6 to 9). In FIG. 14A, a representative graph from at least three independent experiments is shown. In FIGS. 14B and 14C, two-sided unpaired Student's t tests and ANOVA were used where appropriate to assess statistical significance. Graphs depict means SEM; NS, not significant; *$P \leq 0.05$; *$P \leq 0.001$; **$P \leq 0.0001$ relative to vehicle control. In FIG. 14C, delta and statistics are compared to FC-72 vehicle control. In FIGS. 14B-14C, measurements were taken from distinct samples. In FIG. 14A, the same sample for each replicate was measured repeatedly over time.

DETAILED DESCRIPTION OF THE INVENTION

Maintenance of airway surface liquid (ASL) pH is essential to lung physiology and requires a balance between proton export through the nongastric $H^+/K^+$ adenosine triphosphatase ATP12A and bicarbonate secretion through CFTR (3, 4). Respiratory pathogens such as *Pseudomonas aeruginosa* can also contribute to ASL acidification by secreting protons through monocarboxylate lactate-H+co-transporters, a process also countered by bicarbonate secretion in normal airways but not in CF (5). Loss of CFTR thus leads to reduced pH, which increases ASL viscosity and decreases activity of pH-sensitive antimicrobial proteins (3, 6), contributing to the chronic airway infections that cause morbidity and mortality in CF patients (4, 7). Administration of aerosolized bicarbonate or buffers to CF epithelia can alkalinize the ASL and normalize viscosity and antimicrobial activity. However, these effects are transient, with pH returning to baseline values within an hour (3, 8).

Figure 1:
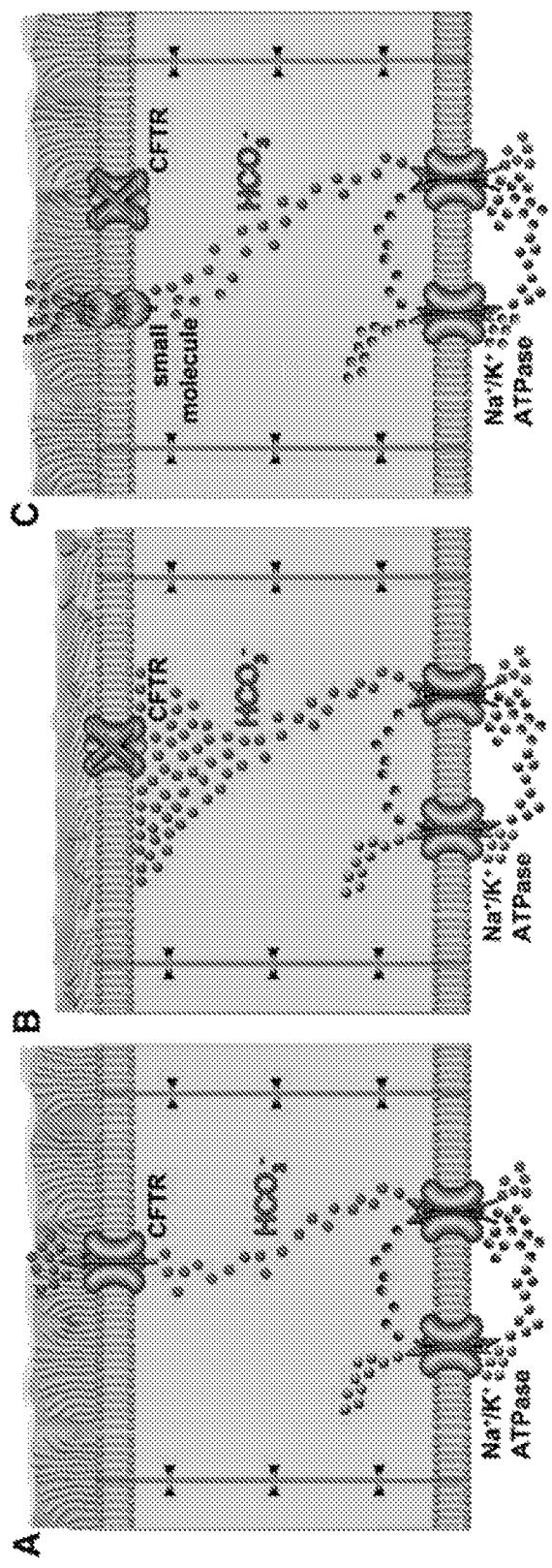
FIG. 1 consists of panels A-F, and generally depicts a model and small molecule probe for genotype-agnostic rescue of CF. Panel A shows a schematic for transepithelial bicarbonate transport in a normal airway epithelial cell. Red spheres represent bicarbonate ions. Green and purple spheres represent sodium and potassium ions, respectively. In panel B, a large transapical gradient of bicarbonate is predicted in CF epithelia lacking the CFTR bicarbonate channel. Panel C shows that a small molecule-based channel is predicted to leverage this transapical gradient to promote bicarbonate secretion into the ASL and thereby restore physiology in CF lung epithelia. Panel D depicts structures of amphotericin B (AmB) and channel-inactivated derivative C35-deoxyamphotericin B (C35deOAmB). Panels E and F show $^{13}$C-NMR spectra of $H^{13}CO_3^-$-loaded POPC/10% cholesterol liposomes show the appearance of a bicarbonate $^{13}$C resonance in the external solution after addition of AmB but not C35deOAmB or DMSO control, demonstrating that AmB is able to facilitate transmembrane bicarbonate efflux. In panel F, a representative graph from at least three independent experiments is shown.
Figure 1:
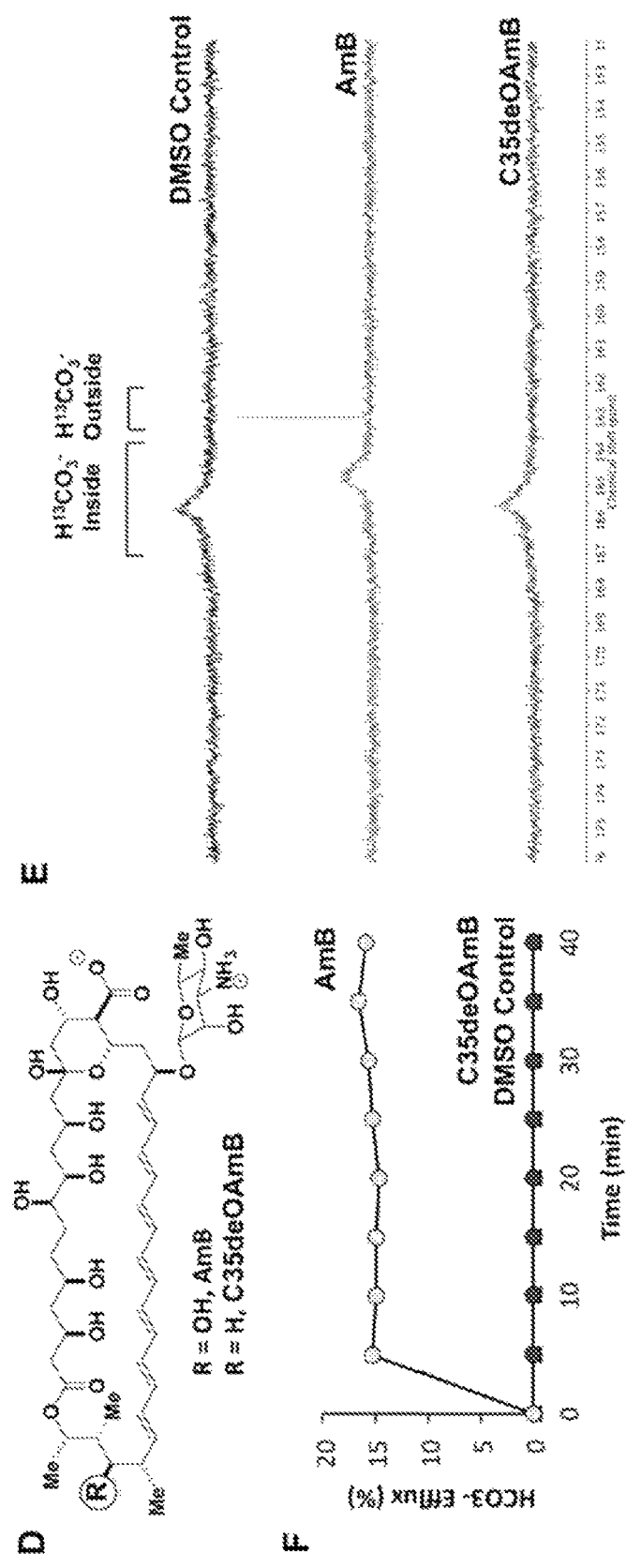

A robust network of pumps and channels on the basolateral membrane, including $Na^+/K^+$ ATPase, normally drives transepithelial bicarbonate transport (FIG. 1, panel A). In the absence of CFTR, bicarbonate ions continue to be driven into cells through the basolateral membrane but apical release is abated, yielding alkalinized intracellular pH (9, 10). This creates a large pH gradient across the apical membrane (FIG. 1, panel B). The inventors surprisingly discovered that small molecule-mediated permeabilization of the apical membrane to bicarbonate increases ASL pH in CF epithelia. Moreover, the inventors determined that this permeabilization functionally integrates with a robust protein network that drives and regulates transepithelial bicarbonate transport, thereby enabling substantial restoration of ASL physiology with an unregulated and relatively unselective surrogate for CFTR (FIG. 1, panel C).

Accordingly, in some embodiments, small molecule ion channels introduced into CF epithelia can restore physiologic features of ASL in CF lung epithelia via proton absorption, bicarbonate secretion, or both. Such a molecular prosthetics approach to CF genotype-independent, i.e., independent of the exact nature of the genetic mutation underlying the reduced CFTR expression or reduced CFTR function in CF.

Amphotericin B (AmB) can permeabilize eukaryotic cells, such as yeast cells, to potassium and other ions. Ermishkin L N et al. (1977) Biochim Biophys Acta 470(3): 357-367. AmB is also highly toxic to yeast, and this toxicity was thought to be inextricably linked to its membrane permeabilization. However, it was found that a synthesized derivative of AmB lacking a single oxygen atom at C35 (C35deOAmB) does not form ion channels, and yet still maintains potent fungicidal activity. Gray K C et al. (2012) Proc Natl Acad Sci USA 109(7): 2234-2239. Further studies revealed that AmB primarily kills yeast by binding and extracting sterols from membranes and is only cytotoxic when the amount of AmB exceeds that of ergosterol. Anderson T M et al. (2014) Nat Chem Biol 10(5): 400-406. Channel formation is not required. This enabled separation of the ion channel activity of AmB from its cell killing effects via administering at low doses and/or pre-complexation with sterols. AmB can restore growth in protein ion channel-deficient yeast. The range of doses for which growth rescue is observed can be extended by more than an order of magnitude when AmB is pre-complexed with the primary sterol in yeast, ergosterol. The non-channel-forming variant C35deOAmB failed to rescue yeast growth at any tested concentration.

In some embodiments, treatment with AmB and a sterol rescues one or more of ASL pH, viscosity, and antimicrobial activity in primary lung epithelia derived from CF.

As will be described in detail here, the cellular mechanisms that drive transepithelial bicarbonate transport in human airways are sufficiently robust to allow imperfect mimicry of CFTR to be sufficient to restore important aspects of ASL physiology in a genotype-agnostic manner. Small molecule channels can be functionally integrated into this robust protein-based bicarbonate transport pathway, and the specific intersection of AmB channels with $Na^+/K^+$ ATPase adds to a growing list of examples where a small molecule surrogate for a missing protein can interface with robust autoregulatory mechanisms in eukaryotic cells (20, 23). The experiments described herein reveal that alternative activities of CFTR that are not replicated by AmB, including regulation of other ion transporters (34, 35), are not required for maintaining ASL pH, viscosity, and antibacterial properties. This result is a remarkable in light of previous reports indicating these alternative activities were likely to be important (34, 35). Collectively, these findings suggest a roadmap for genotype-agnostic rescue of CF using small molecules that promote apical membrane bicarbonate permeabilization. It is notable that AmB is a clinically approved drug that has been safely delivered to the lungs in aerosolized form (32), that AmBisome is a clinically approved mixture containing amphotericin, cholesterol, and other lipids and salts, and that synthetic derivatization of the natural product has recently been shown to modify conductance and selectivity of the corresponding ion channels (33).

Accordingly, in certain embodiments, AmB and a sterol together, for example pre-formed complexes between AmB and a sterol, are effective for increasing the pH of ASL in the lungs of CF patients, thereby improving airway antimicrobial activity and airway protection in these patients. In certain embodiments, the molar ratio of AmB:sterol is in the range from 1:1 to about 1:15.

In certain embodiments, the methods of the invention utilize AmBisome® for Injection (Astellas Pharma US, Inc., Northbrook, IL), which is a sterile, lyophilized preparation of AmB for intravenous infusion. Each vial contains 50 mg of amphotericin B intercalated into a liposomal membrane consisting of approximately 213 mg hydrogenated soy phosphatidylcholine; 52 mg cholesterol, 84 mg distearoylphosphatidyl-glycerol; 0.64 mg alpha tocopherol, together with 900 mg sucrose, and 27 mg disodium succinate hexahydrate as buffer. The molar ratio of AmB to cholesterol for this product is about 1:2.5.

Methods of the Invention

In one aspect, provided herein is a method of treating cystic fibrosis, comprising conjointly administering to a patient in need thereof a therapeutically effective amount of (i) amphotericin B (AmB), or a pharmaceutically acceptable salt or hydrate thereof, and (ii) a sterol or a pharmaceutically acceptable salt thereof, thereby treating the cystic fibrosis.

As used herein, the terms "treat" and "treating" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease.

As used herein, a "patient" refers to a living mammal. In various embodiments, a patient is a non-human mammal, including, without limitation, a mouse, rat, hamster, guinea pig, rabbit, sheep, goat, cat, dog, pig, horse, cow, or non-human primate. In certain embodiments a patient is a human.

As used herein, the phrase "effective amount" refers to any amount that is sufficient to achieve a desired biological effect.

As used herein, the phrase "therapeutically effective amount" refers to any amount that is sufficient to achieve a desired therapeutic effect, e.g., treating cystic fibrosis.

In certain embodiments, the sterol is selected from the group consisting of cholesterol, campesterol, β-sitosterol, 24-isopropylcholesterol, nicasterol, lanosterol, 7-dehydrocholesterol, desmosterol, 4-methylcholestan-8(14),24-dien-3β-ol, gorgosterol, dinosterol, 24S-hydroxycholesterol, 5α-cholestane-hexaol, cycloartenol, stigmasterol, fucosterol, ergosterol, antrosterol, saringosterol, sitosterol, coprostanol, avenasterol, dihydrocholesterol, stigmastanol, campestanol, brassicasterol, and lupeol.

In certain embodiments, the sterol is not cholesterol, and the AmB and the sterol are administered in a molar ratio in the range from about 1:1 to about 1:15.

In certain embodiments, the sterol is not cholesterol and the AmB and the sterol are administered in a molar ratio in the range from about 1:1 to about 1:12. In certain embodiments, the AmB and the sterol are administered in a molar ratio in the range from about 1:1 to about 1:10.

In certain embodiments, the sterol is not cholesterol, and the molar ratio of AmB and sterol is about 1:1 to about 1:14. In certain such embodiments, the molar ratio is about 1:1 to about 1:13. In certain such embodiments, the molar ratio is about 1:1 to about 1:11. In certain such embodiments, the molar ratio is about 1:1 to about 1:9. In certain such embodiments, the molar ratio is about 1:1 to about 1:8. In certain such embodiments, the molar ratio is about 1:1 to about 1:7. In certain such embodiments, the molar ratio is about 1:1 to about 1:6. In certain such embodiments, the molar ratio is about 1:1 to about 1:5. In certain embodiments in which the sterol is not cholesterol, the molar ratio is about 1:2 to about 1:12. In certain such embodiments, the molar ratio is about 1:2 to about 1:10. In certain such embodiments, the molar ratio is about 1:2 to about 1:9. In certain such embodiments, the molar ratio is about 1:2 to about 1:8. In certain such embodiments, the molar ratio is about 1:2 to about 1:7. In certain such embodiments, the molar ratio is about 1:2 to about 1:6. In certain such embodiments, the molar ratio is about 1:2 to about 1:5.

In certain embodiments, the sterol is not cholesterol, and the AmB and the sterol are administered in a molar ratio in the range from about 1:1 to about 1:5. In certain such embodiments, the sterol is not cholesterol, and the AmB and the sterol are administered in a molar ratio in the range from about 1:3 to about 1:5.

Alternatively, in other embodiments, the sterol is cholesterol.

In certain embodiments in which the sterol is cholesterol, the AmB and the sterol are administered in a molar ratio in the range from about 1:1 to about 1:2.5, preferably in a molar ratio is about 1:2.5.

In certain embodiments, the sterol is not ergosterol.

In certain embodiments in which the sterol is ergosterol, the AmB and the sterol are administered in a molar ratio in the range from about 1:1 to about 1:2.5, preferably the molar ratio is about 1:2.5.

In certain embodiments, the AmB and the sterol are administered as separate pharmaceutical compositions.

The separate pharmaceutical compositions of the AmB and the sterol may be administered simultaneously.

Alternatively, the separate pharmaceutical compositions of the AmB and the sterol may be administered at different times. For example, in some embodiments, the sterol is administered within about 5 minutes to within about 168 hours prior to or after the AmB.

In other embodiments, the AmB and the sterol are administered in a single pharmaceutical composition, i.e., the AmB and the sterol are formulated in a single pharmaceutical composition.

In certain embodiments, the AmB and the sterol are present as a complex.

In certain embodiments, the AmB and the sterol are administered systemically.

In certain embodiments, the AmB and the sterol are administered intravenously.

In certain embodiments, the AmB and the sterol are administered to an airway of the subject. For example, the composition can be administered to an airway of the subject by bronchoalveolar lavage (BAL) or by aerosol. As used herein, an "airway of a subject" refers to any or all of the following pulmonary structures: trachea, bronchi, bronchioles, alveoli. In certain embodiments, an airway of a subject refers to a so-called conducting airway, i.e., any or all of the following pulmonary structures: trachea, bronchi, and bronchioles.

In certain embodiments, the AmB and the sterol are administered as an aerosol to an airway of the subject.

Over 1900 different CFTR mutations are found in CF patients, hundreds of which are confirmed to be disease causing through at least five different mechanisms of functional loss. There have been important recent advances in the development of genotype-specific small molecule drugs that bind to certain mutant forms of CFTR and thereby increase its activity. However, nearly half of all CF patients have CFTR genotypes that do not respond to current small molecule treatments. These include major truncations that yield a complete lack of functional CFTR protein and very rare mutations for which the mechanistic underpinnings of functional deficiency are unknown.

In some embodiments, any of the methods disclosed herein treat a mutation class of cystic fibrosis selected from the group consisting of I, II, III, IV, V, VI, U, and combinations thereof. In some embodiments, the mutation class is selected from the group consisting of I/I, I/II, II/U, and U/III.

In some embodiments, any of the methods disclosed herein are genotype-independent treatments.

As used herein, the phrases "genotype-independent" or "genotype-agnostic" refer to any treatment that is independent of the exact nature of the genetic mutation underlying the reduced CFTR expression or reduced CFTR function in CF.

In certain embodiments, the patient has two mutations in the CTFR anion channel, wherein the two mutations are each independently selected from Table 1.

TABLE 1

| CTFR Mutations | | | |
|---|---|---|---|
| R75X | 663delT | 1525 − 1G −> A | 1924del7 |
| CFTRdele1 | G178R | 1525 − 2A −> G | 2055del9 −> A |
| M1V | 675del4 | S466X | 2105 − 2117del13insAGAAA |
| Q2X | E193X | L467P | 2118del4 |
| S4X | 711 + 1G −> T | 1548delG | 2143delT |
| 182delT | 711 + 3A −> G | S489X | G673X |
| CFTRdele2 | 711 + 5G −> A | S492F | 2183AA −> G or 2183delAA −> G |
| CFTRdele2-4 | 712 − 1G −> T | 1609delCA | 2184insA |
| 185 + 1G −> T | H199Y | Q493X | 2184delA |
| CFTRdele2, 3 | P205S | W496X | 2185insC |
| W19X | L206W | I507del | Q685X |
| R75X | W216X | F508del | R709X |
| Q39X | Q220X | 1677delTA | K710X |
| A46D | L227R | V520F | Q715X |

TABLE 1-continued

CTFR Mutations

| | | | |
|---|---|---|---|
| 296 + 1G –> A | 849delG | C524X | 2307insA |
| 296 + 1G –> T | 852del22 | Q525X | L732X |
| CFTRdele3-10, 14b-16 | CFTRdup6b-10 | CFTRdele11 | 2347delG |
| 297 – 1G –> A | 935delA | 1717 – 1G –> A | 2372del8 |
| E56K | Y275X | 1717 – 8G –> A | R764X |
| W57X | C276X | G542X | R785X |
| 306insA | 991del5 | S549R | R792X |
| 306delTAGA | 1078delT | S549N | 2556insAT |
| E60X | 1119delA | G550X | 2585delT |
| P67L | G330X | 1782delA | 2594delGT |
| R75X | R334W | G551S | E822X |
| 365-366insT | 1138insG | G551D | 2622 + 1G –> A |
| G85E | I336K | Q552X | E831X |
| 394delTT | T338I | R553X | W846X |
| L88X | S341P | A559T | Y849X |
| CFTRdele4-7 | 1154insTC | 1811 + 1634A –> G or 1811 + 1.6kbA –> G | R851X |
| CFTRdele4-11 | 1161delC | 1811 + 1G –> C | 2711delT |
| CFTR50kbdel | R347H | R560K | 2721del11 |
| 405 + 1G –> A | R347P | R560T | 2732insA |
| 405 + 3A –> C | R352Q | 1811 + 1G –> A | CFTRdele14b-17b |
| 406 – 1G –> A | 1213delT | 1811 + 1643G –> T | W882X |
| E92K | 1248 + 1G –> A | 1812 – 1G –> A | 2789 + 5G –> A |
| E92X | 1249 – 1G –> A | R560S | 2790 – 1G –> C |
| Q98X | 1259insA | A561E | Q890X |
| 442delA | 1288insTA | V562I | S912X |
| 444delA | W401X | 1824delA | 2869insG |
| 457TAT –> G | 1341 + 1G –> A | 1833delT | Y913X |
| D110H | 1343delG | Y569D | 2896insAG |
| R117C | Q414X | E585X | L927P |
| R117H; 5T | D443Y | 1898 + 1G –> A | 2942insT |
| 541delC | 1461ins4 | 1898 + 1G –> C | 2957delT |
| 574delA | 1471delA | CFTRdele1 3, 14a | S945L |
| 602del14 | A455E | 1898 + 3A –> G | 2991del32 |
| 621 + 1G –> T | 1497delGG | 1898 + 5G –> T | 3007delG |
| 3120G –> A | 3132delTG | H1054D | 3028delA |
| CFTRdele7a, 17b | 3171delC | G1061R | G970R |
| CFTRdele7a-18 | 3171insC | L1065P | CFTRdele16-17b |
| 3120 + 1G –> A | Q1042X | R1066C | L1077P |
| 3121 – 1G –> A | 3271delGG | R1066H | W1089X |
| 3121 – 2A –> G | 3272 – 26A –> G | 3600G –> A | Y1092X |
| 3121 – 977_3499 + 248del2515 | 3600G –> A | CFTRdele19 | W1098X |
| 3349insT | CFTRdele19 | CFTRdele19-21 | M1101K |
| 3659delC | CFTRdele19-21 | 3600 + 2insT | R1102X |
| 3667ins4 | 3600 + 2insT | 3600 + 5G –> A | E1104X |
| S1196X | 3600 + 5G –> A | R1158X | 3500 – 2A –> G |
| 3737delA | R1158X | R1162X | W1145X |
| W1204X | R1162X | W1282X | CFTRdele22-24 |
| 3791delC | 3849G –> A | 4005 + 1G –> A | CFTRdele22, 23 |
| Y122X | 3849 + 4A –> G | CFTRdele21 | Q1330X |
| 3821delT | 3849 + 40A –> G | 4005 + 2T –> C | G1349D |
| I1234V | 3849 + 10kbC –> T | 4010del4 | 4209TGTT –> AA |
| 4326delTC | 3850 – 1G –> A | 4015delA | 4218insT |
| Q1411X | 3850 – 3T –> G | 4016insT | E1371X |
| Q1412X | G1244E | 4022insT | 4259del5 |
| 4374 + 1G –> T | 3876delA | 4021dupT | Q1382X |
| 4374 + 1G –> A | 3878delG | 4040delA | 4279insA |
| 4382delA | S1251N | N1303K | S1255P |
| 4428insGA | L1254X | Q1313X | S1255X |
| 3905insT | D259G | | |

In certain embodiments, the patient has two mutations in the CTFR anion channel, wherein the two mutations are each independently selected from 2184delA, F508del, V520F, 1717-1G→A, E60X, G551D, R553X, and D259G.

In certain embodiments, the patient has a pair of CTFR mutations selected from F508del/F508del, G551D/F508del, R553X/E60X, F508del/1717-1G→A, F508del/2184deA, and D259G/V520F.

In certain embodiments, the patient has a pair of CTFR mutations selected from F508del/F508del, R553X/E60X, F508del/1717-1G→A, F508del/2184delA, and D259G/V520F.

In certain embodiments, the methods of the invention are useful in the treatment of various CF genotypes that are typically non-responsive or minimally-responsive to treatment with conventional CF therapeutics. For example, the V520F allele in patients having the D259G/V520F pair of CTFR mutations is refractory to treatment with ivacaftor.

Accordingly, in certain embodiments, the methods of treating cystic fibrosis described herein are agnostic to CF genotype.

In some embodiments, any of the methods disclosed herein treat refractory or resistant cystic fibrosis. In some embodiments, the cystic fibrosis is refractory or resistant to one or more cystic fibrosis treatments.

In certain embodiments, the cystic fibrosis is refractory to treatment with ivacaftor.

In some embodiments, the method of treating cystic fibrosis further comprises administering to the patient a therapeutically effective amount of an antibiotic.

In certain aspects, provided herein is a method of increasing the pH of airway surface liquid in a patient having cystic fibrosis, comprising administering to a patient having cystic fibrosis a therapeutically effective amount of (i) amphotericin B (AmB) or pharmaceutically acceptable salt or hydrate thereof, and (ii) a sterol or a pharmaceutically acceptable salt thereof, thereby increasing the pH of airway surface liquid in the patient having cystic fibrosis.

The pH of airway surface liquid (ASL) in a subject can be measured using any technique known to those of skill in the art. For example, airway pH can be measured by placing a planar pH-sensitive probe on the tracheal surface. Pezzulo A A et al. (2012) Nature 487: 109-113.

The pH of ASL in a subject is said to be increased when it is measurably greater than the pH of ASL of an untreated subject. In one embodiment the pH of ASL in a subject is said to be increased when it is measurably greater than the pH of ASL of the same subject measured prior to or distant in time from treatment according to a method of the invention.

Such methods of increasing the pH of airway surface liquid are described in Example 2. Remarkably, rescue of ASL pH is observed over a wide range of AmB:sterol concentrations. Accordingly, the method of increasing ASL pH described herein has significant implications for clinical applications.

In certain embodiments, the increase in pH can be 0.01 pH unit to 2.0 pH unit. In certain embodiments, the increase in pH can be 0.01 pH unit to 1.0 pH unit. In certain embodiments, the increase in pH can be 0.01 pH unit to 0.5 pH unit. In certain embodiments, the increase in pH can be 0.01 pH unit to 0.4 pH unit. In certain embodiments, the increase in pH can be 0.01 pH unit to 0.3 pH unit. In certain embodiments, the increase in pH can be 0.01 pH unit to 0.2 pH unit. In certain embodiments, the increase in pH can be 0.01 pH unit to 0.1 pH unit.

In some embodiments, the increase in pH is by apical addition of any one of the compositions disclosed herein.

In some embodiments, the increase in pH of ASL correlates to alkalization of the apical solution. In some embodiments, the alkalization of the apical solution is bicarbonate-dependent. In some embodiments, the increased apical chamber alkalization occurs in the presence of basolateral bicarbonate.

In some embodiments, the increase in ASL pH is not due to increasing CFTR activity/trafficking to the surface or disrupting membrane integrity.

In certain embodiments, the sterol is selected from the group consisting of cholesterol, campesterol, β-sitosterol, 24-isopropylcholesterol, nicasterol, lanosterol, 7-dehydrocholesterol, desmosterol, 4-methylcholestan-8(14),24-dien-3β-ol, gorgosterol, dinosterol, 24S-hydroxycholesterol, 5α-cholestane-hexaol, cycloartenol, stigmasterol, fucosterol, ergosterol, antrosterol, saringosterol, sitosterol, coprostanol, avenasterol, dihydrocholesterol, stigmastanol, campestanol, brassicasterol, and lupeol.

In certain embodiments, the sterol is not cholesterol, and the AmB and the sterol are administered in a molar ratio in the range from about 1:1 to about 1:15.

In certain embodiments, the sterol is not cholesterol and the AmB and the sterol are administered in a molar ratio in the range from about 1:1 to about 1:12. In certain embodiments, the AmB and the sterol are administered in a molar ratio in the range from about 1:1 to about 1:10.

In certain embodiments, the sterol is not cholesterol, and the molar ratio of AmB and sterol is about 1:1 to about 1:14. In certain such embodiments, the molar ratio is about 1:1 to about 1:13. In certain such embodiments, the molar ratio is about 1:1 to about 1:11. In certain such embodiments, the molar ratio is about 1:1 to about 1:9. In certain such embodiments, the molar ratio is about 1:1 to about 1:8. In certain such embodiments, the molar ratio is about 1:1 to about 1:7. In certain such embodiments, the molar ratio is about 1:1 to about 1:6. In certain such embodiments, the molar ratio is about 1:1 to about 1:5. In certain embodiments in which the sterol is not cholesterol, the molar ratio is about 1:2 to about 1:12. In certain such embodiments, the molar ratio is about 1:2 to about 1:10. In certain such embodiments, the molar ratio is about 1:2 to about 1:9. In certain such embodiments, the molar ratio is about 1:2 to about 1:8. In certain such embodiments, the molar ratio is about 1:2 to about 1:7. In certain such embodiments, the molar ratio is about 1:2 to about 1:6. In certain such embodiments, the molar ratio is about 1:2 to about 1:5.

In certain embodiments, the sterol is not cholesterol, and the AmB and the sterol are administered in a molar ratio in the range from about 1:1 to about 1:5. In certain such embodiments, the sterol is not cholesterol, and the AmB and the sterol are administered in a molar ratio in the range from about 1:3 to about 1:5.

Alternatively, in other embodiments, the sterol is cholesterol.

In certain embodiments in which the sterol is cholesterol, the AmB and the sterol are administered in a molar ratio in the range from about 1:1 to about 1:2.5, preferably in a molar ratio is about 1:2.5.

In certain embodiments, the sterol is not ergosterol.

In certain embodiments in which the sterol is ergosterol, the AmB and the sterol are administered in a molar ratio in the range from about 1:1 to about 1:2.5, preferably in a molar ratio is about 1:2.5.

In certain embodiments, the AmB and the sterol are administered as separate pharmaceutical compositions.

The separate pharmaceutical compositions of the AmB and the sterol may be administered simultaneously.

Alternatively, the separate pharmaceutical compositions of the AmB and the sterol may be administered at different times. For example, in some embodiments, the sterol is administered within about 5 minutes to within about 168 hours prior to or after the AmB.

In other embodiments, the AmB and the sterol are administered in a single pharmaceutical composition, i.e., the AmB and the sterol are formulated in a single pharmaceutical composition.

In certain embodiments, the AmB and the sterol are present as a complex.

In certain embodiments, the AmB and the sterol are administered systemically.

In certain embodiments, the AmB and the sterol are administered intravenously.

In certain embodiments, the AmB and the sterol are administered to an airway of the subject. For example, the composition can be administered to an airway of the subject by bronchoalveolar lavage (BAL) or by aerosol. As used herein, an "airway of a subject" refers to any or all of the following pulmonary structures: trachea, bronchi, bronchioles, alveoli. In certain embodiments, an airway of a subject refers to a so-called conducting airway, i.e., any or all of the following pulmonary structures: trachea, bronchi, and bronchioles.

In certain embodiments, the AmB and the sterol are administered as an aerosol to an airway of the subject.

In certain embodiments, the patient has two mutations in the CTFR anion channel, wherein the two mutations are each independently selected from Table 1, shown above.

In certain embodiments, the patient has two mutations in the CTFR anion channel, wherein the two mutations are each independently selected from 2184deA, F508del, V520F, 1717-1G→A, E60X, G551D, R553X, and D259G.

In certain embodiments, the patient has a pair of CTFR mutations selected from F508del/F508del, G551D/F508del, R553X/E60X, F508del/1717-1G→A, F508del/2184deA, and D259G/V520F.

In certain embodiments, the patient has a pair of CTFR mutations selected from F508del/F508del, R553X/E60X, F508del/1717-1G→A, F508del/2184delA, and D259G/V520F.

In certain embodiments, the methods of the invention are useful for increasing the pH of airway surface liquid in a patient having any one of various CF genotypes that are typically non-responsive or minimally-responsive to treatment with conventional CF therapeutics.

Accordingly, in certain embodiments, the methods of increasing ASL pH described herein are agnostic to the patient's CF genotype.

In some embodiments, any of the methods disclosed herein increase ASL pH in patients having refractory or resistant cystic fibrosis. In some embodiments, the cystic fibrosis is refractory or resistant to one or more cystic fibrosis treatments, such as ivacaftor.

In some embodiments, the method further comprises administering to the patient a therapeutically effective amount of an antibiotic.

In certain aspects, provided herein is a method of decreasing the viscosity of airway surface liquid in a patient having cystic fibrosis, comprising administering to a patient having cystic fibrosis a therapeutically effective amount of (i) amphotericin B (AmB) or a pharmaceutically acceptable salt or hydrate thereof, and (ii) a sterol or a pharmaceutically acceptable salt thereof, thereby decreasing the viscosity of airway surface liquid in the patient having cystic fibrosis.

In certain embodiments, the sterol is selected from the group consisting of cholesterol, campesterol, β-sitosterol, 24-isopropylcholesterol, nicasterol, lanosterol, 7-dehydrocholesterol, desmosterol, 4-methylcholestan-8(14),24-dien-3β-ol, gorgosterol, dinosterol, 24S-hydroxycholesterol, 5α-cholestane-hexaol, cycloartenol, stigmasterol, fucosterol, ergosterol, antrosterol, saringosterol, sitosterol, coprostanol, avenasterol, dihydrocholesterol, stigmastanol, campestanol, brassicasterol, and lupeol.

In certain embodiments, the sterol is not cholesterol, and the AmB and the sterol are administered in a molar ratio in the range from about 1:1 to about 1:15.

In certain embodiments, the sterol is not cholesterol and the AmB and the sterol are administered in a molar ratio in the range from about 1:1 to about 1:12. In certain embodiments, the AmB and the sterol are administered in a molar ratio in the range from about 1:1 to about 1:10.

In certain embodiments, the sterol is not cholesterol, and the molar ratio of AmB and sterol is about 1:1 to about 1:14. In certain such embodiments, the molar ratio is about 1:1 to about 1:13. In certain such embodiments, the molar ratio is about 1:1 to about 1:11. In certain such embodiments, the molar ratio is about 1:1 to about 1:9. In certain such embodiments, the molar ratio is about 1:1 to about 1:8. In certain such embodiments, the molar ratio is about 1:1 to about 1:7. In certain such embodiments, the molar ratio is about 1:1 to about 1:6. In certain such embodiments, the molar ratio is about 1:1 to about 1:5. In certain embodiments in which the sterol is not cholesterol, the molar ratio is about 1:2 to about 1:12. In certain such embodiments, the molar ratio is about 1:2 to about 1:10. In certain such embodiments, the molar ratio is about 1:2 to about 1:9. In certain such embodiments, the molar ratio is about 1:2 to about 1:8. In certain such embodiments, the molar ratio is about 1:2 to about 1:7. In certain such embodiments, the molar ratio is about 1:2 to about 1:6. In certain such embodiments, the molar ratio is about 1:2 to about 1:5.

In certain embodiments, the sterol is not cholesterol, and the AmB and the sterol are administered in a molar ratio in the range from about 1:1 to about 1:5. In certain such embodiments, the sterol is not cholesterol, and the AmB and the sterol are administered in a molar ratio in the range from about 1:3 to about 1:5.

Alternatively, in other embodiments, the sterol is cholesterol.

In certain embodiments in which the sterol is cholesterol, the AmB and the sterol are administered in a molar ratio in the range from about 1:1 to about 1:2.5, preferably in a molar ratio is about 1:2.5.

In certain embodiments, the sterol is not ergosterol.

In certain embodiments in which the sterol is ergosterol, the AmB and the sterol are administered in a molar ratio in the range from about 1:1 to about 1:2.5, preferably in a molar ratio is about 1:2.5.

In certain embodiments, the AmB and the sterol are administered as separate pharmaceutical compositions.

The separate pharmaceutical compositions of the AmB and the sterol may be administered simultaneously.

Alternatively, the separate pharmaceutical compositions of the AmB and the sterol may be administered at different times. For example, in some embodiments, the sterol is administered within about 5 minutes to within about 168 hours prior to or after the AmB.

In other embodiments, the AmB and the sterol are administered in a single pharmaceutical composition, i.e., the AmB and the sterol are formulated in a single pharmaceutical composition.

In certain embodiments, the AmB and the sterol are present as a complex.

In certain embodiments, the AmB and the sterol are administered systemically.

In certain embodiments, the AmB and the sterol are administered intravenously.

In certain embodiments, the AmB and the sterol are administered to an airway of the subject. For example, the composition can be administered to an airway of the subject by bronchoalveolar lavage (BAL) or by aerosol. As used herein, an "airway of a subject" refers to any or all of the following pulmonary structures: trachea, bronchi, bronchioles, alveoli. In certain embodiments, an airway of a subject refers to a so-called conducting airway, i.e., any or all of the following pulmonary structures: trachea, bronchi, and bronchioles.

In certain embodiments, the AmB and the sterol are administered as an aerosol to an airway of the subject.

In certain embodiments, the patient has two mutations in the CTFR anion channel, wherein the two mutations are each independently selected from Table 1, shown above.

In certain embodiments, the patient has two mutations in the CTFR anion channel, wherein the two mutations are each independently selected from 2184deA, F508del, V520F, 1717-1G→A, E60X, G551D, R553X, and D259G.

In certain embodiments, the patient has a pair of CTFR mutations selected from F508del/F508del, G551D/F508del, R553X/E60X, F508del/1717-1G→A, F508del/2184deA, and D259G/V520F.

In certain embodiments, the patient has a pair of CTFR mutations selected from F508del/F508del, R553X/E60X, F508del/1717-1G→A, F508del/2184delA, and D259G/V520F.

In certain embodiments, the methods of the invention are useful for decreasing the viscosity of airway surface liquid in a patient having any one of various CF genotypes that are typically non-responsive or minimally-responsive to treatment with conventional CF therapeutics.

Accordingly, in certain embodiments, the methods of decreasing ASL viscosity described herein are agnostic to the patient's CF genotype.

In some embodiments, any of the methods disclosed herein decrease ASL viscosity in patients having refractory or resistant cystic fibrosis. In some embodiments, the cystic fibrosis is refractory or resistant to one or more cystic fibrosis treatments, such as ivacaftor.

In some embodiments, the method further comprises administering to the patient a therapeutically effective amount of an antibiotic.

In accordance with each of the foregoing embodiments, in certain embodiments, the patient is a human.

In accordance with each of the foregoing embodiments, in certain embodiments, the patient is less than 12 years old.

In accordance with each of the foregoing embodiments, in certain embodiments, the patient is at least 12 years old. For example, in certain embodiments, the patient is at least 12 to about 16 years old. In certain other embodiments, the patient is about 16 to about 24 years old. In certain other embodiments, the patient is about 24 to about 30 years old. In certain other embodiments, the patient is about 30 to about 40 years old. In certain other embodiments, the patient is about 40 to about 50 years old. In certain other embodiments, the patient is about 50 to about 60 years old. In certain other embodiments, the patient is about 60 to about 70 years old. In certain other embodiments, the patient is about 70 to about 80 years old.

In some embodiments, any of the methods disclosed herein permeabilize the apical membrane. In some embodiments, any of the methods disclosed herein permeabilize the apical membrane to protons. In some embodiments, any of the methods disclosed herein permeabilize the apical membrane to bicarbonate anions.

Formulations

The formulations used in the invention may be administered in pharmaceutically acceptable solutions, which may routinely contain pharmaceutically acceptable concentrations of salt, buffering agents, preservatives, compatible carriers, adjuvants, and optionally other therapeutic ingredients.

Amphotericin B is commercially available in a number of formulations, including deoxycholate-based formulations and lipid-based (including liposomal) formulations. For purposes of this invention, AmB may be formulated with a sterol. In certain embodiments, such formulation comprises a complex formed between AmB and a sterol.

For use in therapy, an effective amount of the active compound or composition of the invention can be administered to a subject by any mode that delivers the compound or composition to the desired location or surface. Administering the pharmaceutical composition of the present invention may be accomplished by any means known to the skilled artisan. Routes of administration include but are not limited to oral, intravenous, intramuscular, intraperitoneal, subcutaneous, direct injection (for example, into a tumor or abscess), mucosal, inhalation, and topical.

In certain preferred embodiments, the compound or composition is administered systemically. In certain preferred embodiments, the compound or composition is administered intravenously.

In certain preferred embodiments, the compound or composition is administered to an airway. In certain preferred embodiments, the compound or composition is administered as an aerosol to an airway.

Lyophilized formulations are generally reconstituted in suitable aqueous solution, e.g., in sterile water or saline, shortly prior to administration.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, AmBerlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds and compositions for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (α1-antitrypsin); Smith et al., 1989, *J Cin Invest* 84:1145-1146 (a-1-proteinase); Oswein et al., 1990, "Aerosolization of Proteins", Proceedings of Symposium on Respiratory Drug Delivery II, Keystone, Colorado, March, (recombinant human growth hormone); Debs et al., 1988, *J Immunol* 140:3482-3488

(interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569 (incorporated by reference), issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (μm), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

Dosing

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily doses measured in terms of AmB will be, for human subjects, from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

In one embodiment, intravenous administration of a composition of the invention may typically be from 0.1 mg/kg/day to 20 mg/kg/day as measured in terms of AmB. Intravenous dosing thus may be similar to, or advantageously, may exceed maximal tolerated doses of AmB.

For any compound or composition described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

EXAMPLES

Having now described the present invention in detail, the same will be more clearly understood by reference to the following examples, which are included herewith for purposes of illustration only and are not intended to be limiting of the invention.

Cell Lines and Growth Conditions.

NuLi, CuFi-1, and CuFi-4 cells (15) (Welsh Laboratory, University of Iowa) were first grown from cryostock on Thermo Scientific BioLite Cell Culture Treated 75 cm$^2$ flasks, seeded at $1.5 \times 10^4$ cells/cm$^2$, $1 \times 10^3$ cells/cm$^2$, and $1 \times 10^4$ respectively. These flasks were previously coated with 3 mL of 60 µg/mL human placental collagen type VI (Sigma-Aldrich) for a minimum of 18 hours at room temperature, rinsed twice with PBS, and then dried prior to seeding. The cells were cultured with 12 mL of the Bronchial Epithelial Cell Growth Medium (BEGM) BulletKit (Lonza CC-3170), which includes the basal media and eight SingleQuots of supplements (BPE, 2 mL; Hydrocortisone, 0.5 mL; hEGF, 0.5 mL; Epinephrine, 0.5 mL; Transferrin, 0.5 mL; Insulin, 0.5 mL; Retinoic Acid, 0.5 mL; Triiodothyronine, 0.5 mL). The gentamycin-amphotericin B aliquot was discarded and the media was instead supplemented with 50 µg/mL penicillin-streptomycin (Corning Cellgro), 50 µg/mL gentamycin (Sigma-Aldrich G1397), and 2 µg/mL fluconazole (Sigma-Aldrich).

Cells were grown to a 90% confluence at 37° C. and 5% C02 with media changed every 2 days, and then trypsinized with 4 mL of standard 0.25% trypsin with 1 mM EDTA (Gibco 25200-056). Trypsin was inactivated with 10 mL of HEPES Buffered Saline Solution (Lonza CC-5024) with added 1% bovine calf serum. Cells were spun down in an Eppendorf Centrifuge 5430 R at 1500 rpm for 5 minutes and resuspended in BEGM media for passaging.

For culturing onto membrane supports for differentiation, cells were resuspended after centrifugation in Ultroser G media. This is composed of a 1:1 ratio of DMEM:Ham's F-12 supplemented with 2% V/V Ultroser G (Crescent Chemical). The membrane supports used were Millicell 0.4 µm PCF inserts (0.6 cm$^2$) (Millipore PIHP01250) for Ussing chamber studies of candidate ionophores, Falcon® Permeable Support for 6 Well Plate with 0.4 m Transparent PET Membranes (4.67 cm$^2$) (Fisher 08-771) in 6-well companion plates (Fisher 08-771-24) for pH-stat studies, and the Corning Costar 0.4 µm 24-well plate Transwell Clear Polyester Membrane inserts (0.33 cm$^2$) (Corning 3470) for all other studies. These membranes were coated with collagen in the same manner as the flasks detailed above. The Millicell inserts were seeded with 200,000 cells each, the Falcon inserts were seeded with 500,000 cells each, and the Transwell inserts were seeded with 115,000 cells each. These membranes were allowed to mature at an air-liquid interface for a minimum of 14 days to reach full differentiation (15, 52), with the Ultroser G media changed every other day. At full maturation, media was changed every 7 days. For covariate control, membranes used in experiments were close in age and maturation as much as possible.

Primary Cultures of Airway Epithelia.

Airway epithelial cells were obtained from human trachea and bronchi of CF and non-CF specimens obtained from the Iowa Donor Network, either as post-mortem specimens or from tissue deemed not fit for transplant. Studies were approved by the University of Iowa Institutional Review Board. After pronase enzymatic digestion, cells were seeded onto collagen-coated semi-permeable membranes (0.33-1.12 cm$^2$, Corning 3470 polyester, 3460 polyester, 3413 polycarbonate) and grown at an air-liquid interface (52). Airway epithelial cell cultures were analyzed after they had differentiated and at least 14 days post-seeding.

Statistics.

No data were excluded. All data depicts the means SEM with a minimum of 6 biological replicates. D'Agostino & Pearson normality test was used to confirm normal distribution of data. Statistical analysis represents P values obtained from one-way ANOVA or two-sided unpaired or paired student t-test where necessary. In cases where variance was not homogenous between comparison groups, parametric t-test with Welch's correction was performed to account for differences in variance. NS, not significant.

*P<0.05, P≤0.01, *P≤0.001, ****P≤0.0001 unless otherwise noted. Based on pilot experiments, sample sizes were chosen that adequately power each experiment to detect a difference in outcomes between groups. No statistical methods were used to predetermine sample size. Epithelial samples were manually assigned at random into control and experimental groups for each experiment. Animals served as their own controls.

Example 1. Discovery of a Small Molecule that Permeabilizes the Apical Membrane of Differentiated Human Lung Epithelia to Bicarbonate A series of natural products and synthetic compounds reported previously to permeabilize liposomes, cells, and/or nasal epithelia of mice to anions (11-14) were tested using an Ussing chamber and differentiated cultures of airway epithelia derived from an immortalized airway epithelial cell line from a CF patient having the most common ΔF508/ΔF508 genotype (CuFi-1) (15). The clinically approved antifungal natural product amphotericin B (AmB) (FIG. 1, panel D) (16) was exceptionally effective in causing a change in short circuit current. Little or no permeabilization of these same epithelia was observed with any of the other compounds tested. This includes a single-atom-deficient synthetic derivative of AmB (C35deOAmB) that was previously shown to lack ion channel activity (17), thus making this derivative an excellent negative control. The capacity for AmB and C35deOAmB to transport bicarbonate across cholesterol-containing POPC liposomes was tested using an adapted $^{13}C$ NMR-based assay (18). Robust and rapid release of $^{13}C$-labelled bicarbonate from liposomes treated with AmB was observed, but not from those treated with C35deOAmB (FIG. 1, panels E, F).

AmB can be toxic to eukaryotic cells, and this toxicity has long been attributed primarily to membrane permeabilization. Contrary to this model, it was recently determined that AmB primarily kills cells by simply binding sterols; channel formation is not required (17, 19). This enabled the separation of the ion channel activity of AmB from its cell killing effects via administering at low doses and/or pre-complexation with sterols. Using both of these approaches, it was recently found that AmB can restore growth in protein ion channel-deficient yeast (19, 20). The non-channel-forming variant C35deOAmB failed to rescue yeast growth at any tested concentration (17, 20). It was also found that the range of doses for which yeast growth rescue is observed can be extended by more than an order of magnitude when AmB is pre-complexed with ergosterol (19, 20).

Example 2. Examination of Changes in ASL pH

Figure 2:
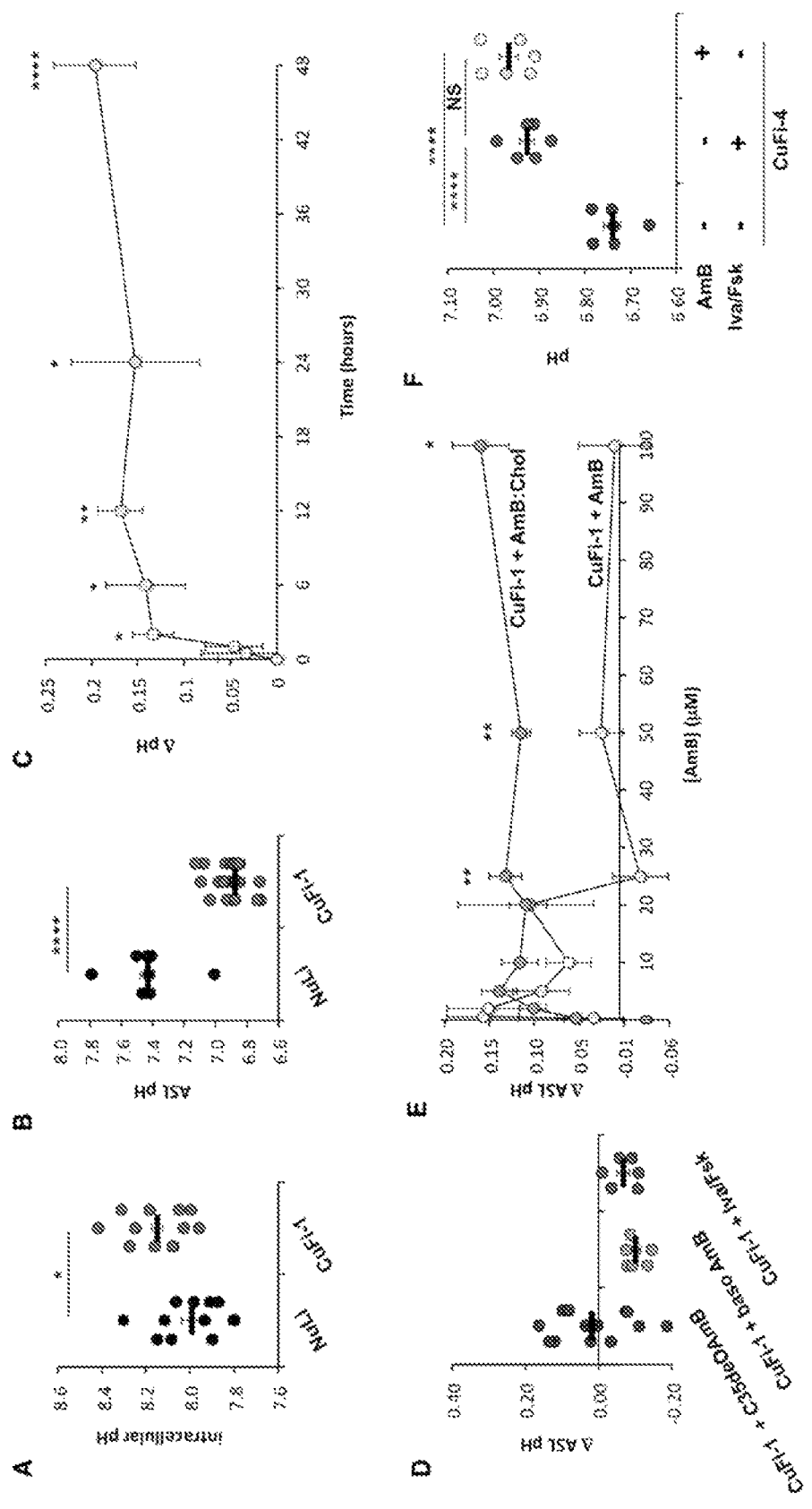
FIG. 2 consists of panels A-F, and generally shows that AmB increases ASL pH in cystic fibrosis cultured airway epithelia. In panel A, the intracellular pH is elevated in CF (CuFi-1) relative to normal (NuLi) cultured airway epithelia (n=12). Panel B shows that the ASL pH is decreased in CF (CuFi-1) relative to normal (NuLi) cultured airway epithelia (n=8 to 31). Panel C is a graph depicting that AmB (2 μM) increases ASL pH relative to an untreated CuFi-1 control over 2 hours and persists for at least 48 hours (n=6 to 28). Panel D shows that an increase in ASL pH was not observed in CuFi-1 monolayers with C35deOAmB (2 μM), basolateral addition of AmB (2 μM), or ivacaftor/forskolin (10 μM) (n=6 to 14). Panel E shows that AmB increases ASL pH in CuFi-1 monolayers at low but not high concentrations. Complexation of AmB with cholesterol extends the window of efficacy to at least 100 uM (n=9 to 31). Panel F shows that both AmB (2 μM) and ivacaftor/forskolin (10 μM) increase ASL pH in CuFi-4 (G551D/ΔF508) monolayers. In panels A-F, graphs depict means SEM; NS, not significant; *P≤0.05; P≤0.01; **P≤0.0001.

With this promising pair of small molecule probes in hand, the prediction that there will be an actionable increase in pH gradient across the apical membrane in CF vs. normal lung epithelia (FIG. 1, panels A, B) was tested. Fluorescent pH dyes (3, 4, 21) confirmed that relative to differentiated epithelial monolayers derived from a normal individual (NuLi) (15), CuFi-1 epithelia have both an increased intracellular pH (FIG. 2, panel A) and a reduced ASL pH (FIG. 2, panel B). Addition of a low concentration of AmB (2 μM) to the apical membrane of CuFi-1 epithelia caused a progressive increase in pH over 2 hours (FIG. 2, panel C). Remarkably, the same increase in pH was then sustained for at least 48 hours. This contrasts sharply with the transient effect on ASL pH caused by aerosolized bicarbonate buffer (3, 8). No increase in pH was observed with apical addition of the non-channel-forming variant C35deOAmB or basolateral addition of AmB (FIG. 2, panel D). AmB-treated CuFi-1 monolayers did not show an increase in short circuit current in response to forskolin/IBMX, showing that the AmB-mediated increase in ASL pH is not due to increasing CFTR activity/trafficking to the surface. AmB addition also did not disrupt membrane integrity.

Figure 5:
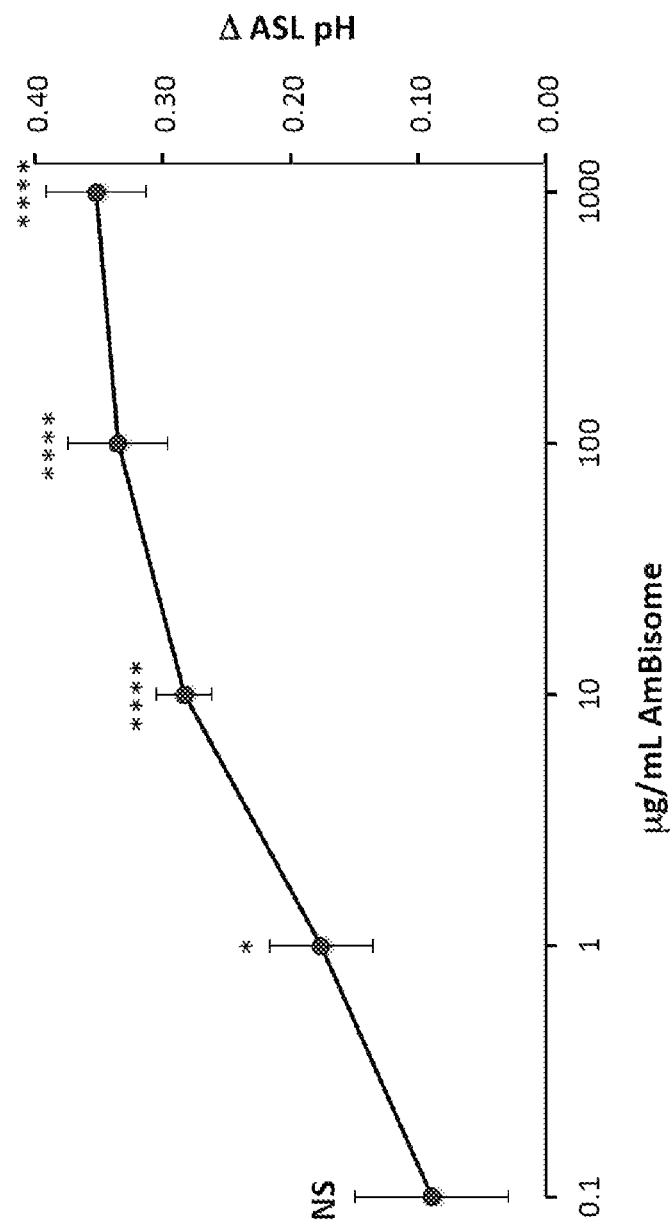
FIG. 5 is a graph depicting the dose-dependent change in airway surface liquid pH with administration of AmBisome® (NS, not significant; *P≤0.05; P≤0.01; *P≤0.001; ****P≤0.0001).
Figure 6:
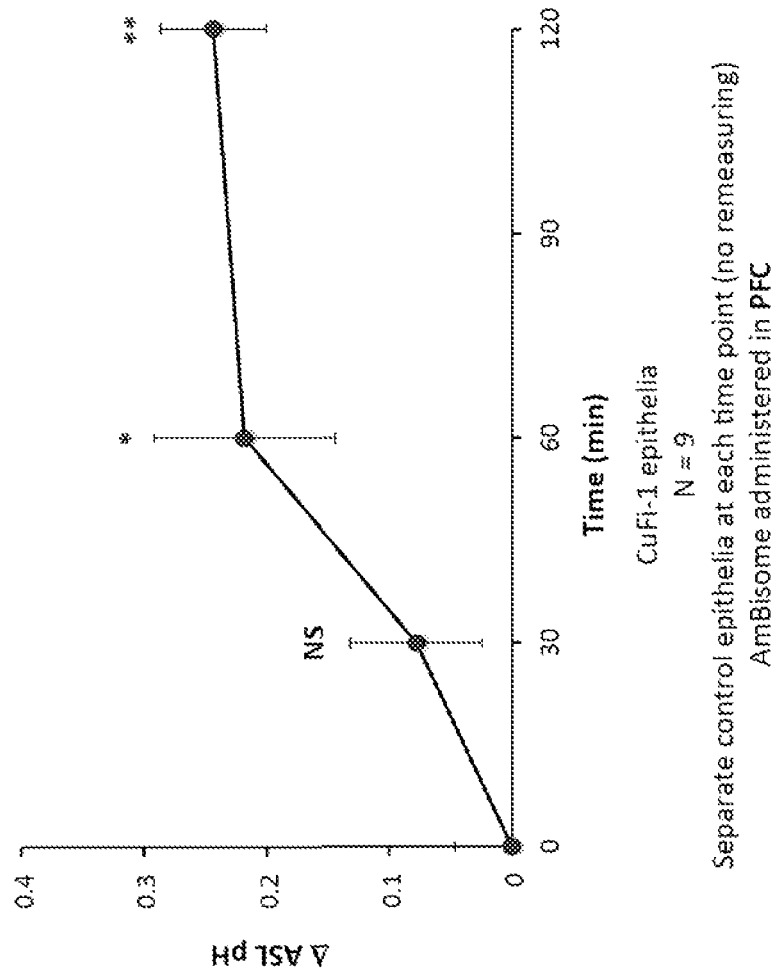
FIG. 6 is a graph depicting change in airway surface liquid pH over time following administration of AmBisome® (NS, not significant; *P≤0.05; P≤0.01; *P≤0.001; ****P≤0.0001).

The AmB-mediated increase in ASL pH in CuFi-1 epithelia reaches a maximum at 2 μM and then decreases at higher concentrations (FIG. 2, panel E). Suspecting that this loss of activity at higher concentrations may be due to toxic cholesterol binding activity (17, 19), a pre-formed an AmB: cholesterol complex was utilized in this concentration dependence experiment. A similar increase in ASL pH was observed and then sustained even up to very high concentrations of AmB (100 μM) (FIG. 2, panel E). The same pattern was previously observed upon progressively increasing CFTR protein expression (22-24). The clinically approved liposomal formulation AmBisome was then tested in this same assay. AmBisome includes AmB and cholesterol at a ratio of 1:2.5 (AmB:cholesterol). Excellent restoration of ASL pH was observed that was sustained up to 100 uM (FIGS. 5 and 6). This invariance of ASL pH with increasingly high concentrations of detoxified channels (FIG. 2, panel E) and the sustained AmB-mediated increase in ASL pH over time (FIG. 2, panel C) collectively suggest that this small molecule may be interfacing with a robust autoregulatory network that controls ASL pH.

Example 3. Investigation of Different CF Genotypes

To investigate whether this AmB-mediated increase in ASL is genotype-agnostic, results using AmB were compared to ivacaftor, which is a genotype-specific treatment. Ivacaftor is a clinically approved small molecule that potentiates the activity of CFTR with a specific mutation (G551D) that causes a gating defect and is present in 24% of CF patients. In primary sinonasal epithelia from a patient with a G551D mutation, ivacaftor increased ASL pH by 0.20 units and decreased viscosity by about 1.5 units relative to untreated controls (25). In large-scale clinical trials with CF patients having at least one G551D allele, ivacaftor had a substantial positive impact, causing a 10% increase in forced expiratory volume and substantially improved body weight, quality of life, and incidence of pulmonary exacerbation (2, 26, 27). This compound does not show benefit in CF epithelia that lack a G551D or similar allele.

As expected, treatment of CuFi-1 epithelia (ΔF508/ΔF508) with ivacaftor showed no increase in ASL pH (FIG. 2, panel D). Consistent with the aforementioned clinical data (2, 26, 27) (25) treating CuFi-4 epithelia (G551D/ΔF508) (25) with ivacaftor caused a 0.2 unit increase in ASL pH (FIG. 2, panel F). In contrast with these genotype-specific results, treatment with AmB increased the ASL pH in both CuFi-1 (FIG. 2, panel B) and CuFi-4 epithelia (FIG. 2, panel F). It is notable that when compared head-to-head, pharmacologic activation of CFTR and apical addition of AmB channels caused the same ~0.2 unit increase in ASL pH (FIG. 2, panel G). The AmB-mediated increase in ASL pH in CuFi-1 was of similar magnitude (FIG. 2, panel B). This further suggests that the small molecule channels may interface with the same endogenous auto-regulatory networks that interface with CFTR to define a maximum ASL pH value.

Example 4. Role of AmB in Promoting Bicarbonate Ion Membrane Efflux

The inventors hypothesized that AmB mediates this increase in ASL pH by promoting the efflux of bicarbonate ions across the apical membrane. AmB is also permeable to protons (20) and thus the promotion of proton absorption represented an alternative or complementary mechanistic possibility.

Figure 3:
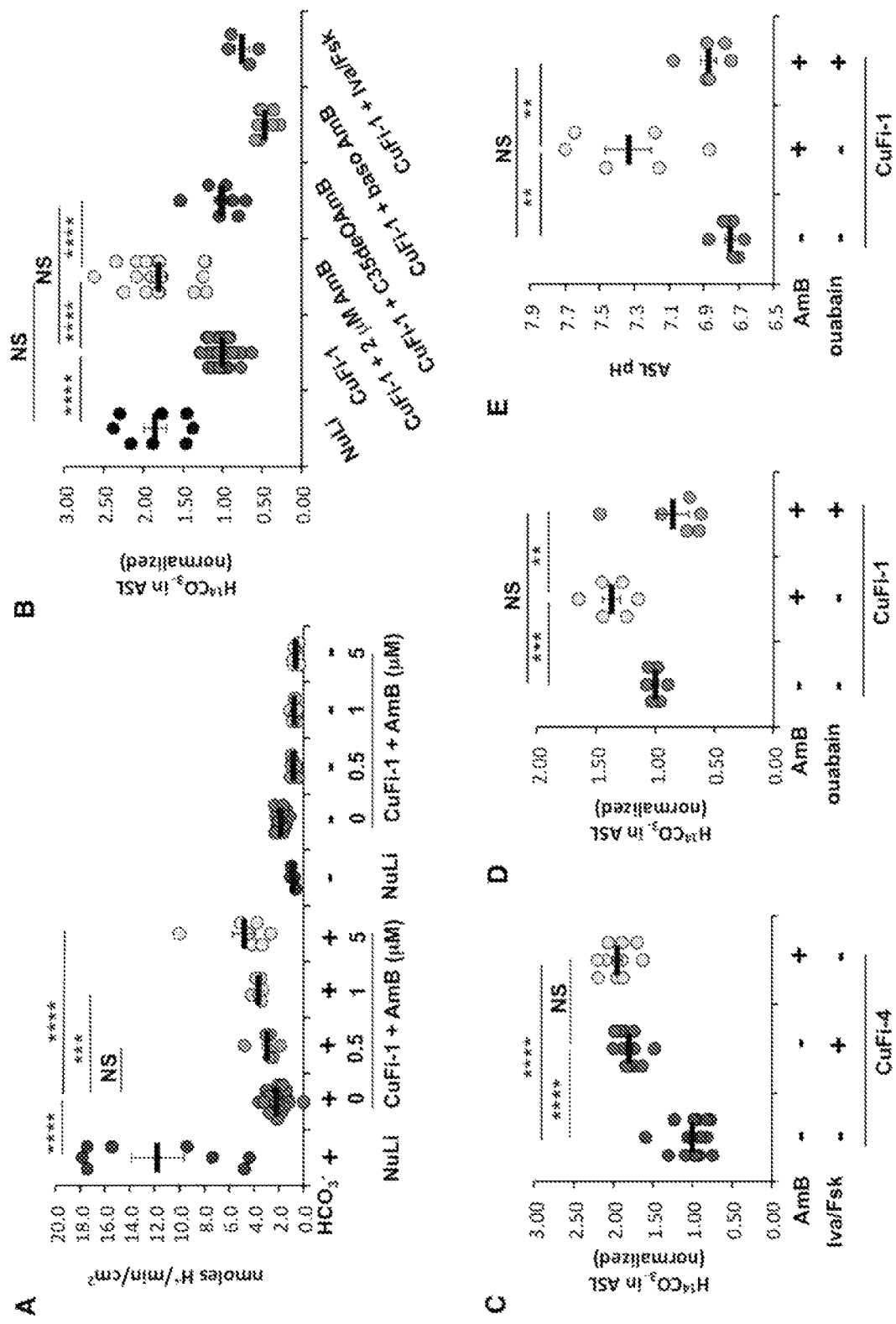
FIG. 3 consists of panels A-E, and generally shows that the AmB-mediated increase of ASL pH is bicarbonate-dependent and $Na^{30}/K^+$ ATPase-dependent. In panel A, the pH-stat titration in NuLi and CuFi-1 monolayers showed a dose-dependent increase in ASL pH with AmB treatment in the presence but not in the absence of basolateral bicarbonate (n=4 to 23). Panel B shows a quantification of basolateral to apical transport of $H^{14}CO_3^{31}$ in CuFi-1 monolayers indicated that AmB (2 μM) restored normal bicarbonate transport, but C35deOAmB (2 μM), basolateral addition of AmB (2 μM), or ivacaftor/forskolin (10 μM) did not (n=4 to 38). Panel C shows that both AmB (2 μM) and ivacaftor/forskolin (10 μM) increase $H^{14}CO3$-transepithelial transport in CuFi-4 (G551D/ΔF508) epithelia (n=10 to 16). In panels D and E, the graphs depict that AmB-mediated increases in transepithelial bicarbonate transport and ASL pH are abrogated by chemical blocking of $Na^+/K^+$ ATPase with ouabain (10 mM) (n=6). In panels A-E, graphs depict means SEM; NS, not significant; P≤0.01; *P≤0.001; ****P≤0.0001.

To probe this, pH-stat experiments were performed in large NuLi and CuFi-1 epithelial monolayers either in the presence of basolateral that contains bicarbonate or is bicarbonate-free (FIG. 3, panel A) (28). As expected, it was observed that a decrease in rate of alkalinization in CuFi-1 vs. NuLi epithelia. In the presence of basolateral bicarbonate (25 mM), addition of AmB increased the rate of apical chamber alkalization of CuFi-1 epithelia in a dose-dependent fashion (FIG. 3, panel A). In contrast, in the presence of bicarbonate free basolateral buffer, no change in rate of apical alkalinization was observed with any tested concentration of AmB (FIG. 3, panel A). These findings are consistent with bicarbonate efflux and not proton influx underlying the AmB-mediated increase in ASL pH.

To further probe whether AmB promotes bicarbonate export, the basolateral buffer was spiked with $^{14}C$ bicarbonate and the amount of radiolabel that reaches the ASL over 10 minutes was quantified. As expected, relative to NuLi, there is a substantial reduction $^{14}C$ bicarbonate transport in CuFi-1 epithelia (FIG. 3, panel B). Apical addition of AmB increased the rate of $^{14}C$ bicarbonate to match that observed in NuLi epithelia (FIG. 3, panel B). The channel-inactivated derivative C35deOAmB and basolateral addition of AmB caused no increase ASL $^{14}C$ bicarbonate (FIG. 3, panel B).

Experiments were conducted to determine whether this AmB-mediated increase in bicarbonate efflux is genotype-agnostic. As expected, ivacaftor increased the rate of bicarbonate efflux in CuFi-4 (FIG. 3, panel C) but not CuFi-1 monolayers (FIG. 3, panel B). In contrast, AmB was effective in both genotypes (FIG. 3, panels B and C). Consistent with the findings for ASL pH (FIG. 2, panel F), pharmacological activation of CFTR and AmB caused the same increase in rate of bicarbonate efflux in CuFi-4 epithelia (FIG. 2, panel C). These results collectively support bicarbonate transport underlying the AmB-mediated increase of ASL pH, and further suggest that the small molecule channels interface with the same auto-regulatory networks that normally include CFTR.

One potential mechanism for such autoregulation is the rate of bicarbonate import through the basolateral membrane, which is primarily driven by a sodium gradient created by $Na^{30}/K^+$ ATPase. The tissue-specific activity of $Na^{30}/K^+$ ATPase is largely regulated by the FXYD family of proteins, and is modulated based on physiological stimuli (29). Previous studies showed that FXYD5 is increased threefold and $Na^{30}/K^+$ ATPase activity is increased twofold in CF vs. non-CF epithelial cells (29, 30). Potassium influx into yeast through Trk transporters is similarly driven by a proton gradient generated by V-ATPase and Pma1, and AmB-mediated growth rescue in Trk-deficient yeast is highly sensitive to V-ATPase or Pma1 chemical inhibition (20). The inventors determined that the AmB-mediated rescue of ASL pH in CF epithelia would be mitigated by chemically blocking $Na^{30}/K^+$ ATPase. Adding ouabain to basolateral buffer of CuFi-1 epithelia in fact abolished the AmB-mediated increase in rate of basolateral-to-apical $^{14}C$ bicarbonate transport and increase in ASL pH (FIG. 3, panels D, E).

Example 5. Application to Primary Human Airway Epithelia

To determine if the capacity for AmB to restore ASL pH in a genotype-agnostic manner translates to primary human airway epithelia, samples from 9 CF patient donors representing a wide range of different CFTR mutations were obtained. These include multiple patients with the most common ΔF508/ΔF508 genotype, a double null genotype (R553X/E60X, patient 6) that results in virtually no CFTR protein produced, a rare splice site allele (ΔF508/1717-1G→A, patient 7), and some rare, uncategorized alleles (ΔF508/c·2052dupA, patient 8 and D259G/V520F, patient 9) (31). The V520F allele in patient 9 is in the same functional category as G551D but is refractory to treatment with ivacaftor (26).

Figure 4:
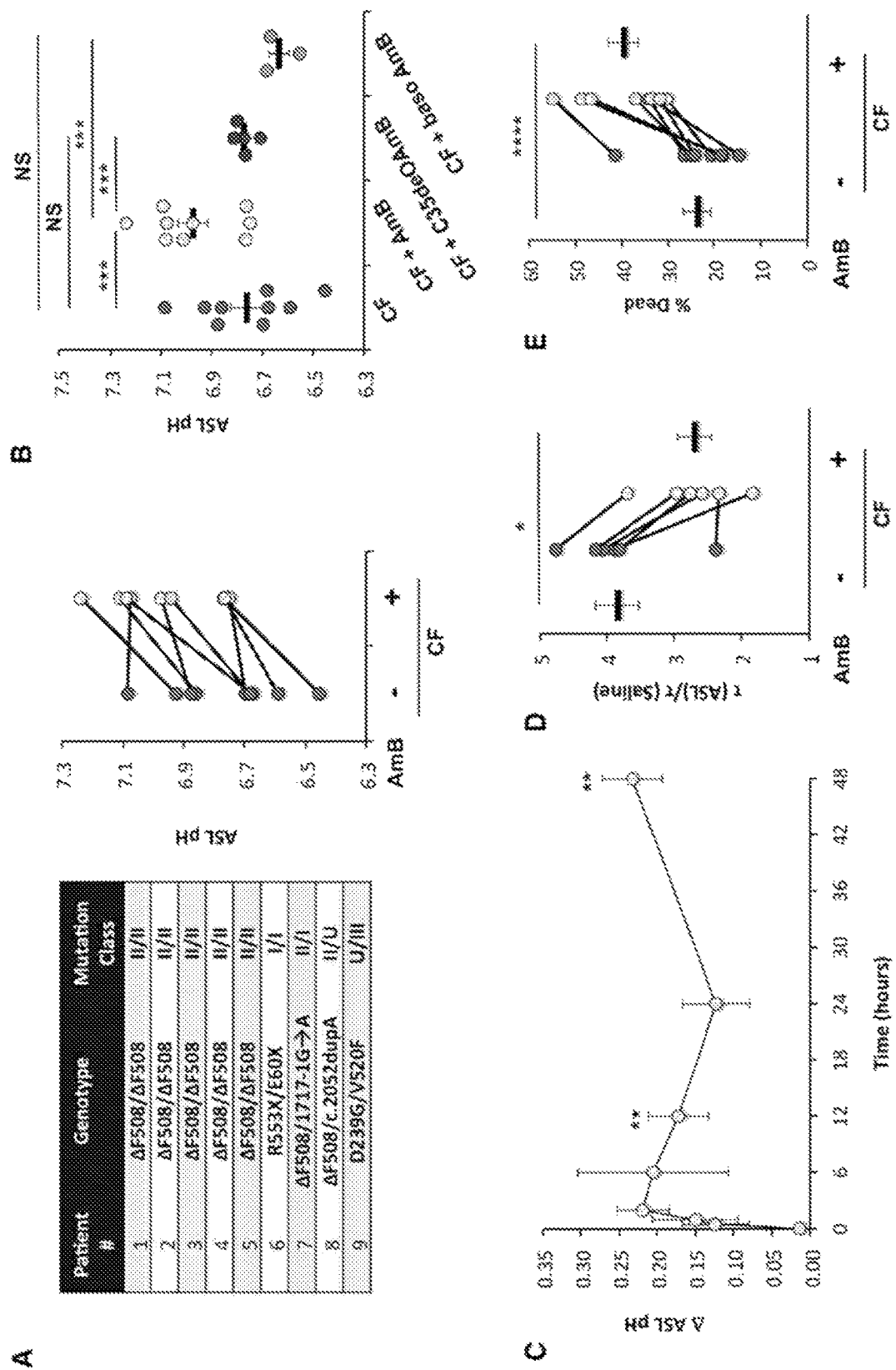
FIG. 4 consists of panels A-E, and generally shows that AmB restores ASL physiology in primary cultured human lung epithelia derived from CF patients with a wide range of CFTR genotypes. Panels A-E generally shows that AmB improved host defenses in primary cultured airway epithelia derived from genetically diverse humans with CF. Panel A is a table listing genotypes and mutation classes of patient donors. An increase in ASL pH was observed with or without apical addition of AmB (2 μM; 48 h) treatment across a wide range of CFTR genotypes in primary cultured airway epithelia derived from 9 humans with CF with a wide range of CFTR mutations (n=9). Panel B is a chart showing that on average, AmB (2 μM) increased ASL pH while C35deOAmB (2 μM) and basolateral addition of AmB (2 μM) did not (n=3 to 9). Panel C shows the average difference in ASL pH by apical addition of AmB (2 μM) as a function of time (n=3 to 9). ASL viscosity as measured by FITC-dextran fluorescence recovery through diffusion ($\tau_{ASL}/\tau_{saline}$) (n=6). Panel D shows the ASL antibacterial activity as measured by the percent of S. aureus killed after exposure to ASL (n=8). Panel E shows the primary CF epithelia with or without apical addition of AmB (2 μM, 48 hours). All compounds were administered in FC-72. In Panels A, C and E, each data point or pair of data points represent an average of epithelia (n=1 to 3) from a different human and the black bar indicates means SEM. In all panels, two-sided unpaired Student's t tests with or without Welch's correction were used where appropriate to assess statistical significance; in panel 3b, * indicate statistical differences as compared to vehicle control; *P≤0.05; P≤0.01; *P≤0.001. In Panels A, D and E, measurements were taken from distinct samples. In Panel C, the same samples for each donor were measured repeatedly over time.

AmB caused an increase in ASL pH across a wide range of different genotypes (FIG. 4, panel A). On average, AmB increased ASL pH by 0.2 pH units, consistent with our results in CuFi-1 and CuFi-4 epithelia (FIG. 2) and consistent with data observed upon treating biopsied airway epithelia from a CF patient with a G551D allele with ivacaftor (25). C35deOAmB and basolateral addition of AmB did not increase ASL pH. AmB treatment had no effect on the pH of non-CF primary cultured epithelia, consistent with selective action in the absence of CFTR and an associated pH gradient. This AmB-mediated increase in the ASL pH is also sustained for at least 48 hours (FIG. 4, panel C), suggesting that autoregulation of bicarbonate transport and pH is likely maintained in these AmB-treated CF patient-derived primary lung epithelia.

Genetically diverse primary cultured human CF epithelia were tested to see whether a single treatment with AmB leads to decreased viscosity in the ASL at the 48 h time point. AmB decreased ASL viscosity across a wide range of patient genotypes (FIG. 4, panel D). The average magnitude of viscosity reduction (~1.5 units) matches that previously observed with ivacaftor-treated primary sinonasal epithelia from a CF patient with a G551D allele (25).

At the same 48 h timepoint the capacity for the ASL of genetically diverse primary CF epithelia was tested without or with AmB treatment to kill bacteria. This was conducted by briefly touching the ASL with a gold grid coated with Staphylococcus aureus, which were confirmed to be insensitive to direct killing by AmB, and then determining the percentage of bacteria killed (3). Treatment with AmB increased antibacterial activity for a diverse range of patient genotypes, including the most common ΔF508/ΔF508 genotype, a double null mutation (R553X/E60X), and some rare uncategorized alleles (ΔF508/c·2052dupA and D259G/V520F). On average, AmB treatment nearly doubled ASL bacterial killing (FIG. 4, panel E), whereas C35deOAmB had no effect.

Next it was tested whether AmB could restore key aspects of airway host defense in differentiated primary cultures of human airway epithelia. Epithelia from 9 donors with CF representing different CFTR mutations was studied, including some that yield no CFTR (FIG. 4, panel A, FIG. 13, panel A). Apical AmB increased ASL pH 0.2 pH units (FIG. 4, panel A) and this effect was sustained for at least 48 hours (FIG. 4, panel C). C35deOAmB and basolateral AmB did not increase ASL pH (FIG. 13, panel B).

ASL viscosity was increased and antibacterial activity was decreased in cultures of CF airway epithelia (4, 7, 48). Non-CF lung epithelia has been shown to have a viscosity 2.5 times that of saline (4). Apical addition of AmB to a panel of genetically diverse primary cultures of CF epithelia decreased ASL viscosity (FIG. 4, panel D, FIG. 13, panel D) to a degree that matched observations with ivacaftor in primary CFTR-G551D sinonasal epithelia (25). Non-CF lung epithelia has been shown to kill 45% of exposed bacteria (4). AmB addition also nearly doubled ASL bacterial killing (FIG. 4, panel E, FIG. 13, panel E), whereas C35deOAmB had no effect (FIG. 13, panel F). AmB alone does not have antibacterial activity against *S. aureus* (FIG. 13, panel G).

Example 6. AmB Increased $H^{14}CO^-$ Secretion and ASL pH in Cultured CF Airway Epithelia Studies have demonstrated that $HCO_3^-$ secretion can enhance airway host defense (4, 36, 40) by increasing ASL pH (3, 4), decreasing ASL viscosity (4, 7, 25), increasing activity of antimicrobial factors (4), maintaining ASL volume homeostasis (41), counteracting local environment acidification by *Pseudomonas aeruginosa* (5), and dissipating proton motive forces in Gram-positive and Gram-negative bacteria (42). The electrochemical gradient across the apical membrane favors $HCO_3^-$ secretion; $HCO_3^-$ is accumulated intracellularly through the integrated activity of $Na^+/K^+$ ATPase (30), $H^+/K^+$ ATPase (4), $K^+$ channels, $Na^+/HCO_3^-$ transporters (NBC), and $Na^+/H^+$ antiporters, as well as carbonic anhydrase (43). Thus, when CFTR opens, $HCO_3^-$ flows into the ASL, raising ASL pH. In the absence of CFTR, intracellular $[HCO_3^-]$ is maintained (44) and this gradient for $HCO_3^-$ exit persists, even increasing as ASL pH falls due to decreased $HCO_3^-$ in the ASL. It was reasoned that the resulting site- and direction-selective build-up of $HCO_3^-$ gradients in the epithelia of people with CF can permit even a relatively unselective small molecule $HCO_3^-$ transporter to restore basolateral-to-apical $HCO_3^-$ flux and thus airway host defenses in CFTR-deficient epithelia. It was recently determined that an unselective small molecule iron transporter is sufficient to restore hemoglobinization in cells and animals that are deficient in iron-transport proteins, and this tolerance for lack of selectivity was mechanistically linked to the site- and direction-selective build-up of iron gradients in membranes that normally host the missing proteins (23).

AmB is a small molecule natural product that forms monovalent ion channels that are unselective for anions vs. cations. It is prescribed as an antifungal, but it has significant toxicity to humans (16). It was recently found that its cytotoxicity is primarily due to sterol extraction from membranes, not channel formation (17, 19). In the presence of lipid bilayers, AmB primarily forms large extramembranous aggregates that extract sterols, likely in dynamic equilibrium with a small amount (<5%) of membrane-inserted ion channels. Cytotoxicity only occurs when the molar ratio of AmB exceeds that of membrane sterol (17, 19). These mechanistic insights allowed its channel activity to be rationally separated from cytotoxicity by using either low concentrations of AmB that form ion channels but do not extract significant amounts of sterol, or by pre-complexing AmB to sterols (17, 19, 20). Although AmB forms ion channels that are permeable to both cations and anions, it restores potassium transport and thus growth in yeast missing the potassium-selective Trk transporters (20). In contrast, a synthetic single atom-deficient derivative that lacks ion channel activity (C35deOAmB) did not (17, 20). It was hypothesized that in the alternative context of a favorable electrochemical gradient for transmembrane $HCO_3^-$ secretion and a robust network of selective pumps and channels for counteracting the transport of cations, apical AmB channels would restore $HCO_3^-$ secretion and thus ASL host defenses to CF epithelia.

AmB is known to transport monovalent anions and cations (FIG. 9, panels A-D), but permeability to $HCO_3^-$ had not been tested. It was found that AmB, but not C35deOAmB, caused $H^{13}CO_3^-$ efflux across cholesterol-containing POPC liposomes (FIG. 9, panels E-H).

Figures 10A, 10B, 10C, 10D, 10E:
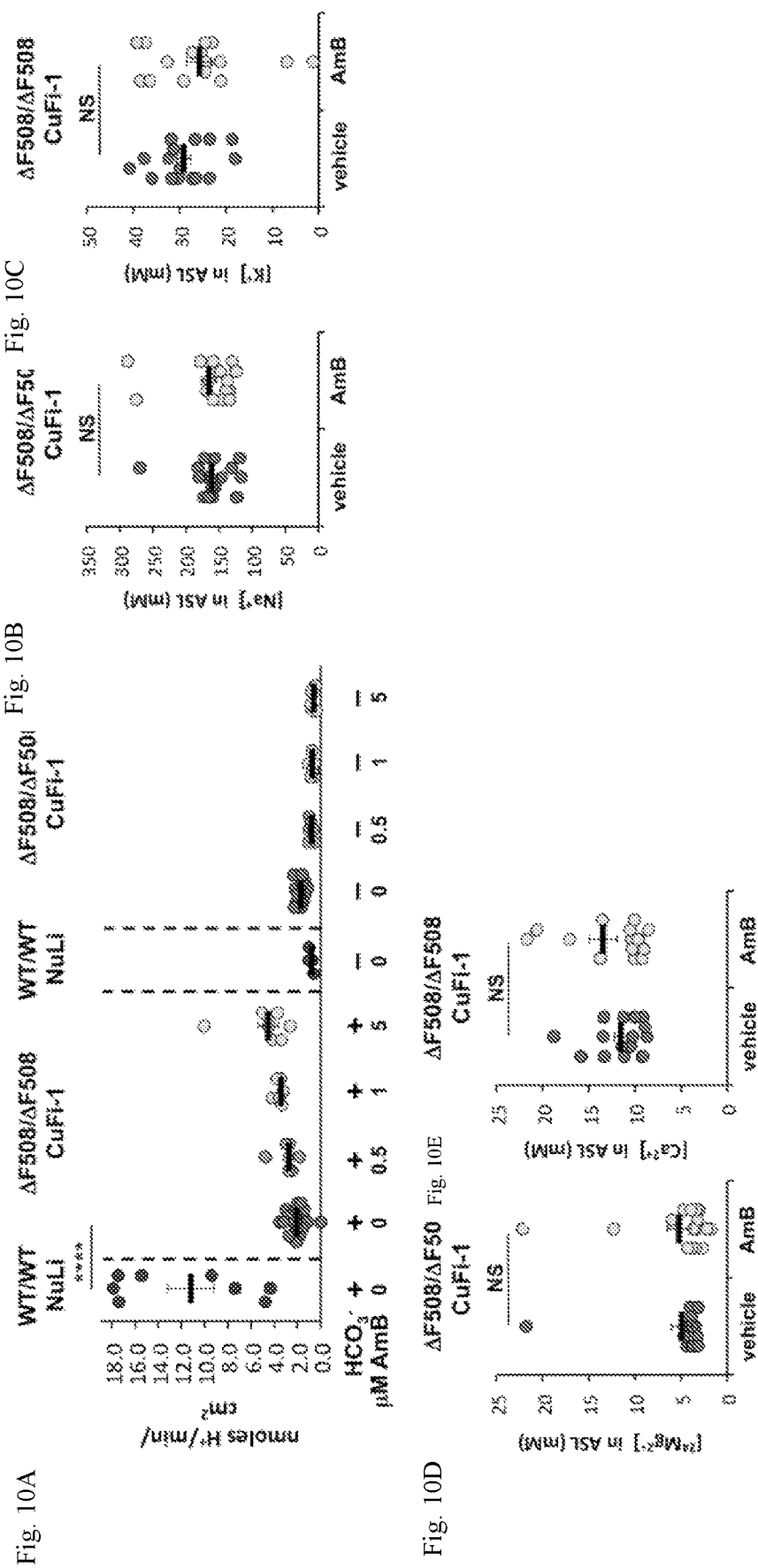
FIGS. 10A-10E generally show that AmB-mediated pH changes are HCO$_3^-$-dependent and do not alter major cation concentrations in the ASL.
Figure 12A:
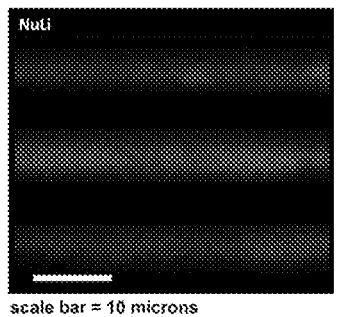
FIGS. 12A-12E generally show that AmB increases ASL height.
Figure 12B:
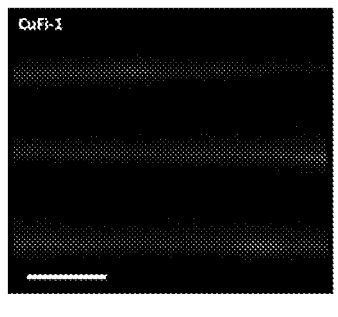
Figure 12C:
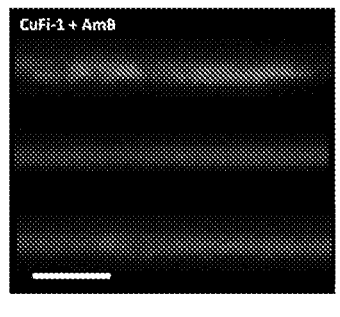
Figure 12D:
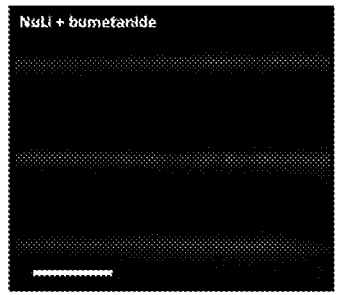
Figure 12E:
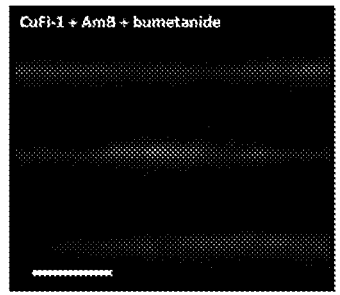

A low concentration of AmB increased ASL pH and $H^{14}CO_3^-$ secretion in CuFi-4 (G551D/ΔF508) CF airway epithelia (FIG. 7, panels A, B). pH-stat experiments indicates that $HCO_3^-$ secretion, rather than proton absorption, primarily underlies the AmB-mediated increase in ASL pH (FIG. 10, panel A). For comparison, ivacaftor was tested, which increased the open state probability of CFTR (47) and improved $FEV_1$ in people with CF carrying a G551D or similar residual function mutation (27). The quantitative effects of ivacaftor on ASL pH and $H^{14}CO_3^-$ secretion were similar to those of AmB (FIG. 7, panels A, B). Though AmB is capable of transporting both anions and cations, ASL concentrations of potassium and sodium were unchanged as compared to vehicle-treated controls (FIG. 10, panels B-E). This can be due to compensatory action of the robust network of cation pumps and channels in airway epithelia.

Ivacaftor does not correct the non-membrane localized ΔF508-CFTR defect (47), and it failed to increase ASL pH or $H^{14}CO_3^-$ secretion in CuFi-1 (ΔF508/ΔF508) epithelia (FIG. 7, panels C, D). In contrast, AmB, which operates independently of the CFTR protein, increased both (FIG. 7, panels C, D). No increase in ASL pH was observed with apical addition of AmB to non-CF (NuLi) epithelia (FIG. 7, panel E), which suggests a dependence upon the presence of pathophysiologic electrochemical gradients. For all experiments herein, AmB was left on the epithelia for the duration of the experiment. AmB progressively increased ASL pH over 2 hours, and the effect was sustained for at least 48 hours in these in vitro experiments (FIG. 7, panel F). The AmB-mediated increase in $H^{14}CO_3^-$ secretion in CuFi-1 epithelia is sustained for at least 7 days (FIG. 11, panels A-C). These results contrast with the transient increase in pH (~15 minutes) produced by aerosolized $NaHCO_3$(8). C35deOAmB and basolateral addition of AmB did not raise ASL pH or increase $H^{14}CO_3^-$ secretion, suggesting that this effect is specific to apically localized AmB channels (FIG. 7, panels C, D).

AmB-treated CuFi-1 epithelia did not respond to chemical activation of CFTR, suggesting that AmB did not promote trafficking of ΔF508 CFTR to the apical membrane (FIG. 11, panels D-I). AmB addition also did not disrupt membrane integrity, as there was no difference in transepithelial electrical resistance ($R_t$) between CuFi-1 epithelia treated with either vehicle, low (2 uM), or high (50 uM) doses of AmB over extended timeframes (FIG. 11, panel J).

Another model of CF links ASL height to pathology (41). At baseline, it was observed that CuFi-1 epithelia had decreased ASL height as compared to NuLi epithelia (FIG. 7, panel G). Apical addition of AmB increased ASL height in CuFi-1 epithelia to match that of NuLi epithelia (FIG. 7, panel G). Vehicle, C35deOAmB, and basolateral AmB did not increase ASL height (FIG. 7, panel G). These results suggest that AmB-based channels restore ASL volume homeostasis despite their lack of ion selectivity.

Secretion of ions through apical channels depends on an electrochemical gradient and that gradient is generated in large part by basolateral membrane transport proteins. It was showed that AmB-mediated growth rescue in Trk-deficient yeast is attenuated by chemical inhibition of $H^+$ ATPases that drive secondary $K^+$ influx (20). A study showed that secretion of chloride ions through peptide channels in the apical membrane of T84 cell monolayers was mitigated by blocking potassium channels on the basolateral membrane (37). It was predicted that inhibiting basolateral transport in CF airway epithelia could similarly prevent AmB-mediated anion secretion. Inhibiting the basolateral $Na^{30}/K^+$ ATPase with ouabain abolished the AmB-mediated increase in ASL pH and $H^{14}CO3$ secretion (FIG. 7, panels H, I). In addition, inhibiting the basolateral $Na^+/K^+/2Cl^-$ transporter with bumetanide decreased ASL height in NuLi epithelia and abolished the AmB-mediated increase in ASL height observed in CuFi-1 epithelia (FIG. 7, panel G, FIG. 12). These results indicate that apical AmB channels functionally interface with endogenous basolateral proteins that drive anion secretion, as AmB-mediated phenomena depend on their activity.

Example 7. AmBisome® Increased ASL pH in Cultured CF Airway Epithelia and in CFTR$^{-/-}$ Pigs It was observed in CuFi-1 epithelia that ASL pH increased and then fell with progressively increasing concentrations of AmB (FIG. 8, panel A). Based on studies in yeast (17, 19, 20), it was hypothesized that a pre-formed AmB:cholesterol complex would mitigate any potential sterol binding-mediated effects that could contribute to the drop in efficacy at higher concentrations of AmB. Accordingly, it was found that a pre-formed AmB:cholesterol (1:5) complex increased ASL pH up to the maximum concentration of AmB tested (100 µM) (FIG. 8, panel A)

Figure 14B:
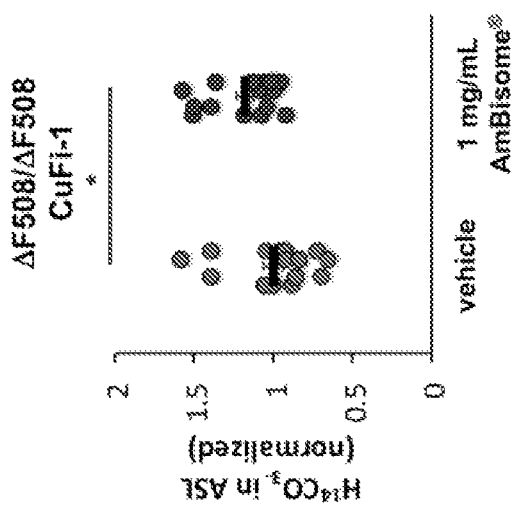
FIGS. 14A-14C generally show that AmBisome® increases transepithelial $H^{14}CO_3^-$ secretion and ASL pH in a time and dose-dependent manner.
Figure 14A:
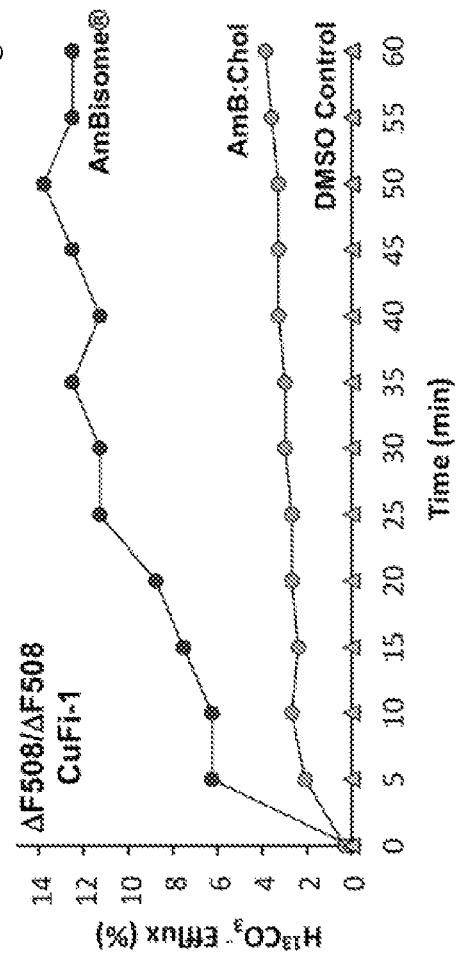
Figure 14C:
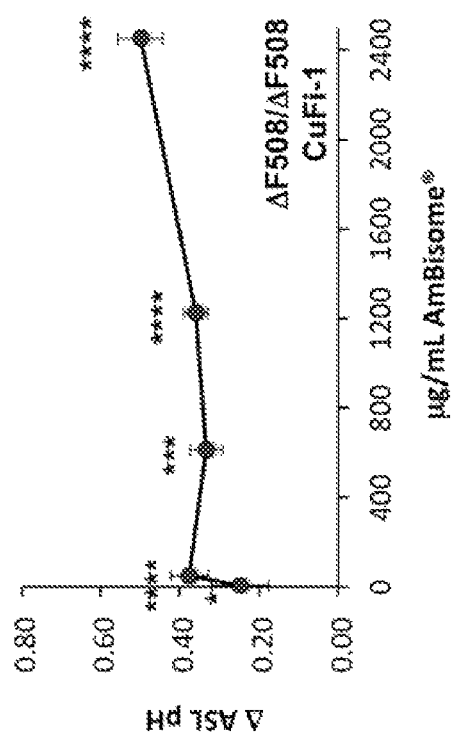

With a goal of testing AmB in vivo, AmBisome® was evaluated, an FDA-approved liposomal formulation that contains AmB and cholesterol in a 1:2.5 ratio (49). AmBisome® increased $H^{13}CO_3^-$ efflux in liposomes (FIG. 14, panel A) and increased ASL pH and $H^{14}CO_3^-$ secretion in CuFi-1 epithelia measured 2 and 48 hours after addition (FIG. 8, panels B, C, FIG. 14, panels B, C). Moreover, AmBisome® increased ASL pH over a large range of AmBisome® concentrations from 6-2450 µg/mL, equivalent to 0.25-100 µM AmB (FIG. 14, panel C).

To assess the ability of AmBisome® to restore ASL pH in vivo, a porcine model of CF was used (8). It was shown that the ASL pH of CFTR$^{-/-}$ pigs does not increase without intervention with aerosolized $HCO_3^-$ or tromethamine buffer (8), and the ASL pH of non-CF pigs is about 7.25 (4). Administrating 60 µL of a 1 mg/mL AmBisome® solution through a tracheal window to 1 cm$^2$ surface of airway increased ASL pH in CFTR$^{-/-}$ pigs (FIG. 8, panel D).

These results indicate that a small molecule ion channel can permeabilize the apical membrane of CF airway epithelia to $HCO_3^-$ and restore ASL pH, viscosity, and antibacterial activity, key components of airway host defenses. CFTR selectively conducts anions, whereas the AmB channel conducts both monovalent anions and cations. Thus, AmB is an imperfect substitute for a CFTR anion channel. However, the robust mechanisms that create an electrochemical driving force for anion secretion establish a setting in which a non-selective channel is sufficient to support anion secretion, the fundamental defect in CF airway epithelia. Other mechanisms may also contribute to the observed AmB-mediated increase in trans-epithelial $HCO_3^-$ transport, such as the coupling of AmB-mediated chloride secretion to $HCO_3^-$ secretion by anion exchangers and other apical membrane protein anion channels (50). These findings reveal a CFTR-independent and thus genotype-independent approach for treating people with CF, including those with nonsense and premature termination codons that produce little or no CFTR. Because this mechanism is distinct, there is also potential for additive effects with CFTR modulators (27, 47). Moreover, AmB is an already clinically approved drug that could be beneficial for people with CF, and AmBisome® is safely delivered to the lungs to treat pulmonary fungal infections without producing significant systemic exposure (49, 51).

Therefore, apical addition of an unselective ion channel-forming small molecule, amphotericin B (AmB), restored $HCO_3^-$ secretion and increased ASL pH in cultured human CF airway epithelia. These effects required the basolateral $Na^{30}/K^+$ ATPase, indicating that apical AmB channels functionally interfaced with this driver of anion secretion. AmB also restored ASL pH, viscosity, and antibacterial activity in primary cultures of airway epithelia from people with CF caused by different mutations, including ones that yield no CFTR, and increased ASL pH in CFTR null pigs in vivo. Thus, an unselective small molecule ion channel can restore CF airway host defenses via a mechanism that is CFTR-independent and therefore genotype-independent.

Example 8. Studies of $Na^+$, $K^+$, $Cl^-$, and $H^{13}CO_3^-$ Efflux from POPC Liposomes (FIG. 9, Panels A-D; FIG. 13, Panel A)

General Information.

Palmitoyl oleoyl phosphatidylcholine (POPC) was obtained as a 25 mg/mL solution in CHCl$_3$ from Avanti Polar Lipids (Alabaster, AL) and was stored at −20° C. under an atmosphere of dry argon and used within 3 months. Cholesterol (Sigma Aldrich) was purified by recrystallization from ethanol. NaH$^{13}$CO$_3$ was obtained as a white solid from Sigma Aldrich. Sodium, potassium, and chloride measurements were obtained using a Denver Instruments (Denver, CO) Model 225 pH meter equipped with the appropriate ion selective probe inside a Faraday cage. Sodium selective measurements were obtained using an Orion micro sodium electrode (Thermo 9811BN). Potassium selective measurements were obtained with an Orion Potassium Sure-Flow Combination Electrode with Waterproof BNC connector (Thermo 9719BNWP). Chloride selective measurements were obtained using an Orion combination chloride electrode (Thermo 9617BNWP). For sodium efflux experiments, measurements were made on 1.5 mL solutions that were magnetically stirred in 7 mL vials incubated at 23° C. For chloride and potassium efflux experiments, measurements were made on 4 mL solutions that were magnetically stirred in 20 mL vials incubated at 23° C. For sodium, potassium, and chloride efflux experiments, the concentration of each ion was sampled every 10 seconds throughout the course of the efflux experiments. $^{13}$C NMR spectra for $HCO_3^-$ efflux experiments were acquired on a Varian Inova 600 µMHz NMR spectrometer with a Varian 5 mm broadband autox probe. The $^{13}$C frequency was set to 150.83 µMHz, and spectral width was 37037 Hz. The instrument was locked on D20. Experimental conditions were: acquisition time, 0.93 s; 300 pulse width, 3.3 µs; relaxation delay, 0.2 s; number of scans, 256; temperature 23° C. The inverse-gated $^{13}$C spectra were collected.

Liposome Preparation.

Prior to preparing a lipid film, this solution was warmed to ambient temperature to prevent condensation from contaminating the solution and degrading the lipid film. 42 mg of solid cholesterol was added to a 20 mL scintillation vial (Fisher Scientific), followed by 14 mL of POPC solution. The solvent was removed with a gentle stream of nitrogen, and the resulting lipid film was stored under high vacuum for a minimum of twelve hours prior to use. For sodium efflux experiments, the film was rehydrated with 2 mL of 250 mM NaHCO$_3$, 40 mM HEPES buffer, pH 7.5 and vortexed vigorously for approximately 3 minutes to form a suspension of multilamellar vesicles (MLVs). For potassium efflux experiments, the film was rehydrated with 2 mL of 250 mM KHCO$_3$, 40 mM HEPES buffer, pH 7.5. For chloride efflux experiments, the film was rehydrated with 2 mL of 250 mM NaCl, 40 mM HEPES buffer, pH 7.5. For HCO$_3^-$ efflux experiments, the film was rehydrated with 2 mL of 250 mM NaH$^{13}$CO$_3$, 40 mM HEPES buffer, pH 7.5 (D20). To obtain a sufficient quantity of large unilamellar vesicles (LUVs), at least two independent lipid film preparations were pooled together for the subsequent formation of LUVs. The lipid suspension was then subjected to 15 freeze-thaw cycles as previously described for H$^{13}$CO$_3^-$ liposomes. Multiple 1 mL preparations were pooled together for the dialysis and subsequent efflux experiments. The newly formed LUVs were dialyzed using Pierce (Rockford, IL) Slide-A-Lyzer MWCO 3,500 dialysis cassettes, 15 mL capacity. The LUV suspension was dialyzed 3 times against 600 mL of 62.5 mM MgSO$_4$, 40 mM HEPES buffer, pH 7.3. The first two dialyses were two hours long, while the final dialysis was performed overnight.

Determination of total phosphorus was adapted (53). The LUV solution was diluted fortyfold with 87 mM Na$_2$SO$_4$ in 40 mM HEPES buffer pH 7.3 (D20). Three 10 μL samples of the diluted LUV suspension were added to three separate 7 mL vials. Subsequently, the solvent was removed with a stream of N$_2$. 450 μL of 8.9 μM H$_2$SO$_4$ was added to each dried LUV film, including a fourth vial containing no lipids that was used as a blank. The four samples were incubated open to ambient atmosphere in a 225° C. aluminum heating block for 25 min and then moved to 23° C. and allowed to cool for 5 minutes at room temperature. After cooling, 150 μL of 30% w/v aqueous hydrogen peroxide was added to each sample, and the vials were returned to the 225° C. heating block for 30 minutes. The samples were then moved to 23° C. and allowed to cool for 5 minutes at room temperature before the addition of 3.9 mL water. Then 500 μL of 2.5% w/v ammonium molybdate was added to each vial, and the resulting mixtures were then vortexed briefly and vigorously five times. Subsequently, 500 μL of 10% w/v ascorbic acid was added to each vial, and the resulting mixtures were then vortexed briefly and vigorously five times. The vials were enclosed with a PTFE lined cap and then placed in a 100° C. aluminum heating block for 7 minutes. The samples were moved to 23° C. and allowed to cool for approximately 15 minutes at room temperature to 23° C. prior to analysis by UV/Vis spectroscopy. Total phosphorus was determined by observing the absorbance at 820 nm and comparing this value to a standard curve obtained through this method and a standard phosphorus solution of known concentration.

Efflux from LUVs.

For sodium, potassium, and chloride efflux experiments, the pooled LUV suspension was diluted to 70 mM with 62.5 mM MgSO$_4$, 40 mM HEPES buffer, pH 7.3. The LUV suspension (1.5 mL for sodium, and 4 mL for chloride and potassium) was added to either a 7 mL or 20 mL vial and gently stirred. The appropriate probe was inserted, and data were collected for one minute prior to addition of AmB. For sodium efflux experiments, 15 μL of either vehicle or AmB (70 μM final concentration, 100× stock solution in DMSO) was added to 1.5 mL of LUV suspension, and data were collected for 10 minutes. To effect complete ion release, 15 μL of a 30% v/v solution of Triton X-100 was added, and data were collected for an additional five minutes. For chloride and potassium efflux experiments, 40 μL of either vehicle or AmB (70 μM final concentration, 100× stock solution in DMSO) was added to 4 mL of LUV suspension, and data were collected for 10 minutes. To effect complete ion release, 40 μL of a 30% v/v solution of triton X-100 was added, and data were collected for an additional five minutes. For HCO$_3^-$ efflux experiments, 5 μL of either DMSO or sterile water vehicle, AmB:Chol, or AmBisome® (70 μM AmB, 100× stock in DMSO or sterile water) was added to 500 μL of the pooled LUV suspension in a New Era (Vineland, NJ) 5 mm NMR sample tube, and consecutive FIDs were acquired for 60 minutes. 5 μL of a 30% v/v solution of triton X-100 was added to effect complete ion release.

The efflux data from each run was normalized to the percent of total ion release from 0 to 100%. For HCO$_3^-$ efflux experiments, after lysis of the liposome suspension, the integration of the signal corresponding to extravesicular HCO$_3^-$ relative to the integration of the $^{13}$C glucose standard was scaled to correspond to 100% efflux. For each experimental run with AmB addition, the signal corresponding to extravesicular HCO$_3^-$ was integrated relative to the $^{13}$C internal standard for each FID. The scaling factor S was calculated for each experiment using the following relationship:

$$\left[\frac{[Ion]_{final}}{[Ion]_{initial}} - 1\right] \cdot S = 100$$

Each data point was then multiplied by S before plotting as a function of time.

Example 9. Studies of H$^+$ Efflux from POPC Liposomes (FIG. 9, Panel D)

Proton efflux from POPC/10% cholesterol liposomes was determined as described above (33).

Example 10. $^{13}$C NMR Studies of H$^{13}$CO$_3^-$ Efflux from POPC Liposomes (FIG. 9, Panels E-H)

Cholesterol-containing POPC lipid films were prepared as described above and stored under high vacuum for a minimum of twelve hours prior to use. The film was then hydrated with 2 mL of 250 mM NaH$^{13}$CO$_3$ in 40 mM HEPES buffer pH 7.5 (D20), and vortexed vigorously for approximately 3 minutes to form a suspension of multilamellar vesicles (MLVs). The lipid suspension was then subjected to 15 freeze-thaw cycles, where the suspension was alternatingly allowed to freeze in a liquid nitrogen bath, followed by thawing in a 50° C. water bath. The resulting lipid suspension was pulled into a Hamilton (Reno, NV) 1 mL gastight syringe and the syringe was placed in an Avanti Polar Lipids Mini-Extruder. The lipid solution was then passed through a 5.00 m Millipore (Billerica, MA) polycarbonate filter 35 times, the newly formed LUV suspension being collected in the syringe that did not contain the original suspension of MLVs to prevent the carryover of MLVs into the LUV solution. To obtain a sufficient quantity of LUVs, two independent 1 mL preparations were pooled together for the dialysis and subsequent efflux experiments. The newly formed LUVs were dialyzed using Pierce (Rockford, IL) Slide-A-Lyzer MWCO 3,500 dialysis cassettes, 3 mL capacity. The LUV suspension was dialyzed 10 times against 300 mL of 87 mM $Na_2SO_4$ in 40 mM HEPES buffer pH 7.3 ($H_2O$) with stirring. The first dialysis was four hours long, while the subsequent nine dialyses were performed for 1 hour. Determination of phosphorous content was performed as described above.

The pooled LUV solution was diluted to 70 mM with 87 mM $Na_2SO_4$, 40 mM HEPES buffer, pH 7.3 (D20), and 0.025% (w/v)$^{13}$C D-glucose (1-$^{13}$C) (Sigma Aldrich) was added as an internal standard. $^{13}$C NMR spectra were acquired on a Bruker Avance III HD 500 μMHz NMR spectrometer equipped with a 5 mm BBFO CryoProbe. The $^{13}$C frequency was set to 125.83 μMHz, and spectral width was 31,512 Hz. The instrument was locked on D20. Experimental conditions were: acquisition time, 0.93 s; 30° pulse width, 3.3 μs; relaxation delay, 0.2 s; number of scans, 256; temperature 23° C.

For each experiment, 1.4 μL of vehicle, AmB, or C35deOAmB (17.5 μM final concentration, stock solution was 100 times more concentrated in DMSO) was added to 140 μL of the liposome suspension. The liposome suspension was immediately transferred to a New Era (Vineland, NJ) micro NMR sample tube (3 mm lower/5 mm upper), and 8 consecutive free induction decays (FIDs) were obtained as described above. For experimental runs with $MnCl_2$, 5 μL of a 50 mM $MnCl_2$ solution was added after the addition of AmB. To effect complete ion release, 10 μL of a 30% (v/v) solution of triton X-100 (Sigma Aldrich) was added to the liposome suspension before data acquisition (15, 54-56).

Example 11. Measurement of ASL pH in Cell Line and Primary Cultures of Airway Epithelia (FIG. 7, Panels A, C, E, G; FIG. 4, Panels A, C, E; FIG. 8, Panels A-B; FIG. 11, Panel D; FIG. 13, Panel C; FIG. 14, Panels B-C)

Small diameter NuLi, CuFi, and primary cultured epithelia were used for this experiment (0.33 cm$^2$). The ratiometric pH indicator SNARF-conjugated dextran (Molecular Probes) was used to measure ASL pH. SNARF powder was suspended via sonication in perfluorocarbon (FC-72, Sigma) and distributed onto the apical surface. ASL pH was measured 2 hr later (3, 4, 25). SNARF was excited at 488 nm and emission was recorded at 580 nm and 640 nm using a Zeiss LSM 800 microscope at 40× water immersion for cell line cultures and a Zeiss LSM 510 microscope for primary cultures. To generate a standard curve for pH determination, SNARF was dissolved in colorless pH standards and fluorescence ratios were converted to pH.

Agents tested in this assay were first lyophilized into powder and then suspended in the appropriate volume of perfluorocarbon (FC-72, Sigma) and sonicated for 1 minute to suspend. AmBisome should not be sonicated; instead, the fine powder was suspended by vortexing. 20 μL of this suspension was administered onto the surface of cultured airway epithelia (0.33 cm$^2$) at the following approximate concentrations in suspension:
- amphotericin B 0.25-100 μM
- amphotoricin B-cholesterol complex 0.5-100 μM
- C35deOamphotericin B 2 μM (17)
- 10 mM ouabain (inhibition of Na$^+$/K$^+$ ATPase) (9)
- 10 μM forskolin/10 μM ivacaftor (25)
- AmBisome 0.25-2450 μg/mL In all experiments, ASL pH of compound-treated epithelia was measured compared the results to vehicle-treated epithelia.

For apical AmB administration, cultured airway epithelia were incubated for 30 min-48 hrs at 37° C. before measurement of ASL pH. For AmB-cholesterol complex and C35deOAmB administration, cultured airway epithelia were incubated for 48 hrs at 37° C. before measurement of ASL pH. To test the effect of Na$^{3O}$/K$^+$ ATPase inhibition, AmB was administered 47 hours prior to 10 mM ouabain addition, and cultured airway epithelia were incubated for an additional 1 hr at 37° C. before measurement of ASL pH. For 10 μM ivacaftor/10 μM forskolin administration, cultured airway epithelia were incubated for 2 hrs at 37° C. before measurement of ASL pH (25). For basolateral AmB administration, a 2 mM stock of AmB in DMSO was diluted 1000-fold to a final concentration of 2 μM in USG media. The basolateral media of cultured airway epithelia was replaced with the AmB-containing USG media and incubated for 48 hrs at 37° C. before measurement of ASL pH.

Example 12. pH-Stat Titration of NuLi and CuFi Monolayers (FIG. 4, Panel A)

Large diameter NuLi and CuFi-1 cultured epithelia were used for this experiment (4.67 cm$^2$). These cultures were mounted in a dual-channel Ussing chamber (Warner U2500) using the culture cup insert for Transwell adapter, 24 mm (U9924T-24). The membranes were bathed at 37° C. on the apical side with a buffer-free solution (140 mM NaCl, 2 mM KCl, 2 mM $CaCl_2$), and 1 mM $MgCl_2$, 15 mM dextrose, gassed with air) and on the basolateral side with either a $HCO_3^-$ buffer (120 mM NaCl, 25 mM $NaHCO_3$, 5 mM KCl, 2 mM $CaC_2$, 1.2 mM $MgCl_2$, 13.75 $NaH_2PO_4$, 5.6 mM dextrose, pH adjusted to 7.0) or a $HCO_3^-$-free buffer (140 mM NaCl, 2 mM KCl, 2 mM $CaCl_2$), 1 mM $MgCl_2$, 10 mM HEPES, 5 mM dextrose, pH adjusted to 7.0). A microdiameter pH electrode (89231-590) and temperature probe (Radiometer Analytical T201 Temperature Sensor, E51M001) and titration burette attached to a Hach TIM856 NB pH/EP/Stat pH-STAT Titrator (R41T028) were inserted into the apical chamber. The basolateral chamber was covered with the chamber lid to prevent gas exchange. The pH electrode was then calibrated using known pH solutions (Hach, S11M002, S11M004, S11M007).

The apical pH was titrated to a target pH of 6.0 using 1 mM HCl as titrant (min speed 0.25 mL/min, max speed 0.35 mL/min) (28, 57-59). Acid titration was measured over 20 minutes to establish a baseline value for the cultured epithelia (max speed 2 mL/min). Both apical and basolateral bathing solutions were then removed. A stock solution of AmB in DMSO was added to a final concentration of 0.5, 1, or 2 μM in an aliquot of buffer-free solution and added to the apical chamber, and the basolateral chamber was replaced with fresh $HCO_3^-$ or $HCO_3^-$ free buffer. The apical pH was once again titrated to a target pH of 6.0 using 1 mM HCl as titrant. Acid titration was then measured over another 20 minutes to evaluate AmB-mediated pH change in the apical solution.

Data was plotted as nmoles of H$^+$ titrated in per minute, and the slope of this curve was divided by the area of the culture (4.67 cm$^2$) to obtain the rate of acid titration (nmoles H$^+$/min/cm$^2$).

Example 13. Determination of ASL Na$^+$, K$^+$, Mg$^{2+}$, and Ca$^{2+}$ Concentrations in CuFi-1 Monolayers (FIG. 10, Panels B-E)

Small diameter CuFi-1 cultured epithelia were used for this experiment (0.33 cm$^2$). 24 hours prior to the start of experiment, the apical side of all cultured epithelia was rinsed three times with 200 μL warm PBS to remove excess mucus. Fresh USG media was added to the basolateral membrane. CuFi-1 epithelia were treated with either perfluorocarbon (FC-72) vehicle or 2 μM AmB suspended in FC-72, and incubated at 37° C. for 48 hours. 0.1 μL capacity microcapillary tubes (Drummond Scientific NC1453214) were placed into 200 μL pipette tips (Denville Scientific P1122). 48 hours after AmB addition, the microcapillary tubes were gently touched around the edge of the apical membrane of each epithelial culture insert until completely filled with ASL via capillary action. After collecting 0.1 μL of ASL, a p200 pipette was used to push the entire sample into 15 μL of molecular biology grade water (Corning 46-000-CM). The sample was then quantitatively transferred to a 15 mL capacity conical vial by washing 3 times with 50 μL molecular biology grade water.

Quantification of sodium, magnesium, potassium, and calcium was accomplished using inductively coupled plasma mass spectrometry (ICP-MS) of acidified samples. Each sample was diluted to a final volume of 5 mL with 1.0% $HNO_3$ (v/v) in double distilled water. Quantitative standards were made using a mixed Na, Mg, K, and Ca standard at 100 μg/mL of each element (Inorganic Ventures, Christiansburg, VA, USA) which were combined to create a 100 ng/mL mixed element standard in 1.0% nitric acid (v/v).

ICP-MS was performed on a computer-controlled (QTE-GRA software) Thermo iCapQ ICP-MS (Thermo Fisher Scientific, Waltham, MA, USA) operating in KED mode and equipped with a ESI SC-2DX PrepFAST autosampler (Omaha, NE, USA). Internal standard was added inline using the prepFAST system and consisted of 1 ng/mL of a mixed element solution containing Bi, In, $^{6}$Li, Sc, Tb, Y (IV-ICPMS-71D from Inorganic Ventures). Online dilution was also carried out by the prepFAST system and used to generate calibration curves consisting of 5000, 1000, 500, 100, and 50 ng/mL Na, Mg, K, Ca. Each sample was acquired using 1 survey run (10 sweeps) and 3 main (peak jumping) runs (40 sweeps). The isotopes selected for analysis were $^{23}$Na, $^{24}$Mg, $^{39}$K, $^{44}$Ca' and $^{89}$Y (chosen as internal standards for data interpolation and machine stability). Instrument performance is optimized daily through autotuning followed by verification via a performance report (passing manufacturer specifications).

Example 14. $H^{14}CO_3^-$ Transport Across NuLi and CuFi Monolayers (FIG. 7, Panels B, D, H; FIG. 4, Panel D; FIG. 11, Panels A-C; FIG. 13, Panel B)

Small diameter NuLi and CuFi cultured epithelia were used for this experiment (0.33 cm$^2$). $^{14}$C-labeled sodium $HCO_3^-$ was obtained as a sterile 35.7 mM aqueous solution pH 9.5 (MP Biomedicals 0117441H). All experiments were run less than 2 months post seeding. Fresh USG media was added to the basolateral side prior to experimentation. The apical membrane was treated with 20 μL of vehicle, AmB, or ivacaftor/forskolin as a suspension in perfluorocarbon-72 (Sigma Aldrich), and the cultured epithelia were incubated for 48 hours, 7 days, 14 days, or 28 days at 37° C. in a 5% C02 atmosphere. After the end of the treatment period, 5 μL of a 1.4 mM $H^{14}CO_3^-$ stock solution in USG media was added to the basolateral media. The cultured epithelia were then incubated at 37° C. for 10 minutes. After 10 minutes, the apical membrane of the cultured epithelia was immediately washed with 200 μL of PBS. The ASL wash and a 200 μL aliquot of the basolateral media were diluted in scintillation cocktail and analyzed via liquid scintillation counting (23).

Example 15. Ussing Chamber Studies of NuLi and CuFi Monolayers (FIG. 1, Panels E-G)

To assess the presence of membrane-expressed CFTR, differentiated cultures of NuLi and CuFi-1 epithelia grown on Corning Costar 0.4 μm 24-well plate Transwell Clear Polyester Membrane inserts were used. NuLi and CuFi-1 epithelia were treated with 20 μL of perfluorocarbon (FC-72, Sigma) vehicle or 2 μM amphotericin B (AmB) sonicated into a suspension in FC-72. After 48 hours of incubation, the epithelia were mounted in a dual-channel Ussing chamber (Warner U2500) using the culture cup insert for Transwell adapter, 6.5 mm (Warner U9924T-06) and bathed on both the apical and basolateral sides with a $HCO_3^-$ solution (120 mM NaCl, 25 mM $NaHCO_3$, 5 mM KCl, 2 mM $CaC_2$, 1.2 mM $MgC_2$, 13.75 mM $NaH_2PO_4$, pH 7.0) at 37° C. and gassed with compressed air. Dextrose was added to this solution immediately prior to experiments to a final concentration of 5.6 mM. Epithelial sodium channel (ENaC) and calcium-activated chloride channel (CaCC) were inhibited by apical addition of 1 μM amiloride and 1 μM DIDS (4,4'-disothiocyanostilbene-2,2'-disulfonic acid), respectively, to achieve a baseline for permeabilization. 10 μM forskolin/100 μM IBMX (3-isobutyl-1-methylxanthine) added apically was used to activate CFTR, and 1 μM $CFTR_{inh}$-172 was used to inhibit CFTR. Each successive addition of reagent was allowed approximately 10 minutes to equilibrate before the addition of the next reagent (15).

Example 16. Measurement of Transepithelial Electrical Resistance ($R_t$) (FIG. 1, Panel H)

Small diameter CuFi-1 cultured epithelia were used for this experiment (0.33 cm$^2$) Cultured epithelia were treated with FC-72 vehicle, 2 and 50 μM AmB administered in perfluorocarbon (FC-72, Sigma) for 48 hours, 7 days, or 28 days. 200 μL of fresh USG media was placed on the apical side of the epithelia. Transepithelial electrical resistance ($R_t$) was then measured using a Millicell® ERS-2 Voltohmmeter across the apical and basolateral sides of the epithelia in a snaking pattern for two technical replicates per biological replicate.

Example 17. Lactate Dehydrogenase (LDH) Assay (FIG. 1, Panel I)

Small diameter CuFi-1 cultured epithelia were used for this experiment (0.33 cm$^2$). An LDH Cytotoxicity Assay Kit (Cayman Chemical) was used to determine if AmB is toxic to CuFi-1 airway epithelia. Prior to treatment, media was removed from the basolateral side of epithelia and replaced with 500 □L of fresh USG media. Cultured epithelia were then treated with FC-72 vehicle, 2 and 50 μM AmB administered in perfluorocarbon (FC-72, Sigma) for 48 hours, 7 days, or 28 days. 48 hours prior to the end of each experiment time frame, basolateral media was changed again and 20 DL of 10% Triton X-100 solution was added to the apical surface to elicit maximum release. On the day of the experiment, assay reagents were prepared according to kit instructions and 500 □L of USG media was added to three empty wells in a 24-well plate for background control. Culture inserts were removed from the wells and 250 □L of LDH Reaction Solution was added to each well. The plate was then gently shaken on an orbital shaker for 30 minutes at 37° C. Absorbance was read at 490 nm using a plate reader. % cytotoxicity was calculated as follows:

$$\% \text{ Cytotoxicity of test sample} = \left[ \frac{\begin{array}{c}(\text{Experimental value } A490) - \\ (\text{Background value } A490)\end{array}}{\begin{array}{c}(\text{Maximum value } A490) - \\ (\text{Background value } A490)\end{array}} \right] \cdot 100$$

Example 18. Airway Surface Liquid (ASL) Height Assay (FIG. 7, Panel F; FIG. 12)

ASL height was studied using an established fluorescent dye assay (60, 61). Small diameter NuLi and CuFi-1 cultured epithelia were used for this experiment (0.33 cm$^2$). 24 hours prior to the start of experiment, the apical side of all cultured epithelia was rinsed three times with warm PBS to remove excess mucus. NuLi epithelia were treated with perfluorocarbon (FC-72) vehicle or 500 □M basolateral bumetanide in DMSO vehicle applied to the media, and CuFi epithelia were treated with 20 μL vehicle, 0.005, 0.5, or 50 μM AmB, or 0.5 μM C35deOAmB suspended in perfluorocarbon (FC-72, Sigma), with or without 500 μM basolateral bumetanide in DMSO vehicle applied to the media and incubated for 24 hours at 37° C. After 24 hours, 2.5 μL of a 2 mg/mL 70 kDa Texas Red-dextran conjugate (Molecular Probes) solution in PBS was added to the apical side of the epithelia, followed by 100 μL of FC-770 to prevent evaporation. Then the culture support was placed on top of 100 μL of PBS on a 10 mm glass bottom Fluorodish for imaging (World Precision Instruments). Epithelia were imaged immediately after dye addition and again at 24 hours to examine dye absorption. Three Z-stack images per membrane were taken on an Zeiss LSM700 confocal microscope at 40× oil immersion. These images were analyzed using ImageJ (62) to determine the average ASL height in the center 1300 pixels of each image. Images were smoothed, converted to 8-bit, and thresholded to most accurately represent the red area. The parameters for Analyze Particles were particles from 1-Infinity μm$^2$ in size and from 0%-100% circularity. Height was determined by dividing the area output in pixels by the known 1300 pixel width and converted to microns using the known scaling factor of 0.49 □m/pixel.

Example 19. Viscosity of AmB-Treated Primary Cultures of Airway Epithelia (FIG. 8, Panel C)

ASL viscosity in airway epithelial cultures was determined (7, 25). Small diameter primary cultured epithelia were used for this experiment (0.33 cm$^2$). The apical surface was not washed for at least 2 weeks before study. Cultured epithelia were treated with 2 □M AmB administered in perfluorocarbon (FC-72, Sigma) for 48 hours. FITC-dextran (70 kD, Sigma) was then administered to the apical surface of epithelia as a dry powder 2 hrs before measurement of viscosity. FRAP was assayed in a humidified chamber at 37° C. using a Zeiss LSM 510 μMETA microscope. Images were acquired until maximal recovery was reached. At least 6 recovery curves from different locations in each culture were acquired and averaged to obtain data for one epithelial culture. The time constant (saline) was calculated by regression analysis from fluorescence recovery curves. Viscosity is expressed relative to the time constant of saline (τASL/τsaline).

Example 20. Antibacterial Activity of AmB-Treated Primary Cultures of Airway Epithelia (FIG. 8, Panel D, FIG. 14, Panels F-G)

*Staphylococcus aureus*-coated gold grids were used to measure antibacterial activity of airway epithelial cultures (3, 4). Small diameter primary cultured epithelia were used for this experiment (0.33 cm$^2$). Bacteria-coated gold TEM grids were placed onto the apical surface of airway epithelia for 1 min after 48 hours of perfluorocarbon (FC-72, Sigma), 2 μM AmB, or 2 μM C35deOAmB treatment. As controls, bacteria-coated grids were also placed in saline or AmB in FC-72 laid over saline to simulate the administration method for 1 minute. After removal, bacteria on the grids were assessed for viability using Live/Dead BacLight Bacterial Viability assay (Invitrogen). Viability was determined in 4-6 fields to determine the percentages of dead bacteria.

Example 21. Animals for Study (FIG. 4, Panel E)

Female and male newborn pigs with targeted disruption of the CFTR gene CFTR$^{-/-}$ were studied, generated from mating CFTR$^{+/-}$ pigs. Pigs were obtained from Exemplar Genetics. The University of Iowa Animal Care and Use Committee approved all animal studies.

Example 22. Measurement of ASL pH in CFTR$^{-/-}$ Pigs (FIG. 4, Panel E)

ASL pH was measured in pigs in vivo (3, 8). To administer AmBisome in pig trachea, pigs were initially sedated with ketamine (Ketaject, Phoenix; 20 mg/kg, i.m. injection) and anesthetized using propofol (Diprivan, Fresenius Kabi; 2 mg/kg, i.v. injection). The trachea was surgically exposed and accessed anteriorly, and a small anterior window was cut through the tracheal rings. To mimic physiologic conditions, data was obtained in a 100% humidified chamber at 37° C. and constant 5% C02.

For the first CFTR$^{-/-}$ pig, a baseline ASL pH measurement was taken for about 8 minutes before 60 μL of 100 μg/mL AmBisome® in FC-72 was administered to the tracheal window. ASL pH was continually measured for 60 minutes. Then, 60 μL of 1 mg/mL of AmBisome® was administered to the tracheal window and pH was continually measured for another 60 minutes. For the second CFTR$^{-/-}$ pig, a baseline ASL pH measurement was taken for about 8 minutes before 60 μL of FC-72 vehicle was administered to the tracheal window as an internal control. ASL pH was continually measured for another 30 minutes. Then, 60 L of 1 mg/mL of AmBisome® was administered to the tracheal window and continuous measurements were then taken for 106 minutes. For the third and fourth CFTR$^{-/-}$ pigs, a baseline ASL pH measurement was taken for about 10 minutes. Then, 60 μL of 1 mg/mL of AmBisome® in FC-72 was administered to the tracheal window and continuous measurements were taken for 120 minutes.

REFERENCES CITED

1. F. Ratjen et al., Cystic fibrosis. *Nature Reviews Disease Primers* 1, 15010 (2015).
2. B. P. Trivedi, Cystic fibrosis foundation opens drug discovery lab. *Science* 353, 1194-1195 (2016).

3. A. A. Pezzulo et al., Reduced airway surface pH impairs bacterial killing in the porcine cystic fibrosis lung. *Nature* 487, 109-113 (2012).
4. V. S. Shah et al., Airway acidification initiates host defense abnormalities in cystic fibrosis mice. *Science* 351, 503-507 (2016).
5. J. P. Garnett et al., Hyperglycaemia and *Pseudomonas aeruginosa* acidify cystic fibrosis airway surface liquid by elevating epithelial monocarboxylate transporter 2 dependent lactate-H+ secretion. *Sci Rep* 6, 37955 (2016).
6. M. H. Abou Alaiwa et al., pH modulates the activity and synergism of the airway surface liquid antimicrobials beta-defensin-3 and LL-37. *Proc Natl Acad Sci USA* 111, 18703-18708 (2014).
7. X. X. Tang et al., Acidic pH increases airway surface liquid viscosity in cystic fibrosis. *J Clin Invest* 126, 879-891 (2016).
8. M. H. Abou Alaiwa et al., Repurposing tromethamine as inhaled therapy to treat CF airway disease. *JCI Insight* 1, (2016).
9. D. C. Devor et al., Bicarbonate and chloride secretion in Calu-3 human airway epithelial cells. *J Gen Physiol* 113, 743-760 (1999).
10. N. M. Walker et al., Cellular chloride and bicarbonate retention alters intracellular pH regulation in Cftr KO crypt epithelium. *Am J Physiol Gastrointest Liver Physiol* 310, G70-80 (2016).
11. B. Shen, et al., A synthetic chloride channel restores chloride conductance in human cystic fibrosis epithelial cells. *PLoS One* 7, e34694 (2012).
12. A. V. Koulov et al., Chloride transport across vesicle and cell membranes by steroid-based receptors. *Angew Chem Int Ed Engl* 42, 4931-4933 (2003).
13. C. Jiang et al., Partial correction of defective Cl(-) secretion in cystic fibrosis epithelial cells by an analog of squalamine. *Am J Physiol Lung Cell Mol Physiol* 281, L1164-1172 (2001).
14. M. El-Etri, J. Cuppoletti, Metalloporphyrin chloride ionophores: induction of increased anion permeability in lung epithelial cells. *Am J Physiol* 270, L386-392 (1996).
15. J. Zabner et al., Development of cystic fibrosis and noncystic fibrosis airway cell lines. *Am J Physiol Lung Cell Mol Physiol* 284, L844-854 (2003).
16. L. N. Ermishkin, et al., Properties of amphotericin B channels in a lipid bilayer. *Biochim Biophys Acta* 470, 357-367 (1977).
17. K. C. Gray et al., Amphotericin primarily kills yeast by simply binding ergosterol. *Proc Natl Acad Sci USA* 109, 2234-2239 (2012).
18. J. T. Davis et al., Using small molecules to facilitate exchange of bicarbonate and chloride anions across liposomal membranes. *Nat Chem* 1, 138-144 (2009).
19. T. M. Anderson et al., Amphotericin forms an extramembranous and fungicidal sterol sponge. *Nat Chem Biol* 10, 400-406 (2014).
20. A. G. Cioffi, et al., Restored Physiology in Protein-Deficient Yeast by a Small Molecule Channel. *J Am Chem Soc* 137, 10096-10099 (2015).
21. H. Kawase et al., A dipeptidyl peptidase-4 inhibitor ameliorates hypertensive cardiac remodeling via angiotensin-II/sodium-proton pump exchanger-1 axis. *J Mol Cell Cardiol* 98, 37-47 (2016).
22. V. S. Shah et al., Relationships among CFTR expression, HCO(3)(-) secretion, and host defense may inform gene- and cell-based cystic fibrosis therapies. *Proc Natl Acad Sci USA* 113, 5382-5387 (2016).
23. A. S. Grillo, et al., Restored iron transport by a small molecule promotes gut absorption and hemoglobinization. *Science*, (2017) in press.
24. E. Gouaux, R. Mackinnon, Principles of selective ion transport in channels and pumps. *Science* 310, 1461-1465 (2005).
25. E. H. Chang et al., Medical reversal of chronic sinusitis in a cystic fibrosis patient with ivacaftor. *Int Forum Allergy Rhinol* 5, 178-181 (2015).
26. F. Van Goor, et al., Effect of ivacaftor on CFTR forms with missense mutations associated with defects in protein processing or function. *Journal of Cystic Fibrosis* 13, 29-36 (2014).
27. B. W. Ramsey et al., A CFTR Potentiator in Patients with Cystic Fibrosis and the G551D Mutation. *New England Journal of Medicine* 365, 1663-1672 (2011).
28. D. Y. Cho, et al., Acid and base secretion in freshly excised nasal tissue from cystic fibrosis patients with DeltaF508 mutation. *Int Forum Allergy Rhinol* 1, 123-127 (2011).
29. T. J. Miller, P. B. Davis, FXYD5 modulates Na+ absorption and is increased in cystic fibrosis airway epithelia. *Am J Physiol Lung Cell Mol Physiol* 294, L654-664 (2008).
30. D. Peckham, et al., $Na^+/K^+$ ATPase in lower airway epithelium from cystic fibrosis and non-cystic-fibrosis lung. *Biochem Biophys Res Commun* 232, 464-468 (1997).
31. J. Hull, S. Shackleton, A. Harris, Abnormal mRNA splicing resulting from three different mutations in the CFTR gene. *Hum Mol Genet* 2, 689-692 (1993).
32. D. Xia et al., Aerosolized amphotericin B as prophylaxis for invasive pulmonary aspergillosis: a meta-analysis. *International Journal of Infectious Diseases* 30, 78-84 (2015).
33. S. A. Davis et al., C3-OH of Amphotericin B Plays an Important Role in Ion Conductance. *J Am Chem Soc* 137, 15102-15104 (2015).
34. W. B. Guggino, The Cystic Fibrosis Transmembrane Regulator Forms Macromolecular Complexes with PDZ Domain Scaffold Proteins. *Proceedings of the American Thoracic Society* 1, 28-32 (2004).
35. B. K. Berdiev, Y. J. Qadri, D. J. Benos, Assessment of the CFTR and ENaC association. *Mol Biosyst* 5, 123-127 (2009).
36. Quinton, P. M. The neglected ion: $HCO_3^-$. *Nature medicine* 7, 292-293 (2001).
37. Wallace, D. P. et al. A synthetic channel-forming peptide induces Cl(-) secretion: modulation by Ca(2+)-dependent K(+) channels. *Biochim Biophys Acta* 1464, 69-82 (2000).
38. Wainwright, C. E. et al. Lumacaftor-Ivacaftor in Patients with Cystic Fibrosis Homozygous for Phe508del CFTR. *New England Journal of Medicine* 373, 220-231, doi:doi:10.1056/NEJMoa1409547 (2015).
39. Oliver, K. E., Han, S. T., Sorscher, E. J. & Cutting, G. R. Transformative therapies for rare CFTR missense alleles. *Curr Opin Pharmacol* 34, 76-82, doi:10.1016/j.coph.2017.09.018 (2017).
40. Poulsen, J. H., Fischer, H., Illek, B. & Machen, T. E. Bicarbonate conductance and pH regulatory capability of cystic fibrosis transmembrane conductance regulator. *Proceedings of the National Academy of Sciences of the United States of America* 91, 5340-5344 (1994).
41. Garland, A. L. et al. Molecular basis for pH-dependent mucosal dehydration in cystic fibrosis airways. *Proceedings of the National Academy of Sciences* 110, 15973-15978 (2013).

42. Farha, M. A., French, S., Stokes, J. & Brown, E. D. Bicarbonate alters bacterial susceptibility to antibiotics by targeting the proton motive force. *ACS infectious diseases* (2017).
43. Lee, M. G., Ohana, E., Park, H. W., Yang, D. & Muallem, S. Molecular mechanism of pancreatic and salivary gland fluid and $HCO_3$ secretion. *Physiol Rev* 92, 39-74, doi:10.1152/physrev.00011.2011 (2012).
44. Widdicombe, J., Welsh, M. & Finkbeiner, W. Cystic fibrosis decreases the apical membrane chloride permeability of monolayers cultured from cells of tracheal epithelium. *Proceedings of the National Academy of Sciences* 82, 6167-6171 (1985).
45. Rogers, C. S. et al. Disruption of the CFTR gene produces a model of cystic fibrosis in newborn pigs. *Science* 321, 1837-1841, doi:10.1126/science.1163600 (2008).
46. Stoltz, D. A. et al. Cystic fibrosis pigs develop lung disease and exhibit defective bacterial eradication at birth. *Sci Transl Med* 2, 29ra31, doi:10.1126/scitranslmed.3000928 (2010).
47. Van Goor, F. et al. Rescue of CF airway epithelial cell function in vitro by a CFTR potentiator, VX-770. *Proceedings of the National Academy of Sciences* 106, 18825-18830, doi:10.1073/pnas.0904709106 (2009).
48. Derichs, N., Jin, B.-J., Song, Y., Finkbeiner, W. E. & Verkman, A. Hyperviscous airway periciliary and mucous liquid layers in cystic fibrosis measured by confocal fluorescence photobleaching. *The FASEB Journal* 25, 2325-2332 (2011).
49. Monforte, V. et al. Nebulized liposomal amphotericin B prophylaxis for *Aspergillus* infection in lung transplantation: pharmacokinetics and safety. *J Heart Lung Transplant* 28, 170-175, doi:10.1016/j.healun.2008.11.004 (2009).
50. Saint-Criq, V. & Gray, M. A. Role of CFTR in epithelial physiology. *Cell Mol Life Sci* 74, 93-115, doi:10.1007/s00018-016-2391-y (2017).
51. Rijnders, B. J. et al. Aerosolized liposomal amphotericin B for the prevention of invasive pulmonary aspergillosis during prolonged neutropenia: a randomized, placebo-controlled trial. *Clinical infectious diseases* 46, 1401-1408 (2008).
52. Karp, P. H. et al. An in vitro model of differentiated human airway epithelia. Methods for establishing primary cultures. *Methods Mol Biol* 188, 115-137, doi:10.1385/1-59259-185-x:115 (2002).
53. Chen, P. S., Toribara, T. Y. & Warner, H. Microdetermination of Phosphorus. *Analytical Chemistry* 28, 1756-1758, doi:10.1021/ac60119a033 (1956).
54. Andrews, N. J. et al. Structurally simple lipid bilayer transport agents for chloride and bicarbonate. *Chemical Science* 2, 256-260, doi:10.1039/COSC00503G (2011).
55. Busschaert, N. et al. Tripodal transmembrane transporters for bicarbonate. *Chem Commun (Camb)* 46, 6252-6254, doi:10.1039/cOcc01684e (2010).
56. Busschaert, N. et al. Synthetic transporters for sulfate: a new method for the direct detection of lipid bilayer sulfate transport. *Chemical Science* 5, 1118-1127, doi:10.1039/C3SC52006D (2014).
57. Cho, D. Y., Hajighasemi, M., Hwang, P. H., Illek, B. & Fischer, H. Proton secretion in freshly excised sinonasal mucosa from asthma and sinusitis patients. *Am J Rhinol Allergy* 23, e10-13, doi:10.2500/ajra.2009.23.3389 (2009).
58. Fischer, H. & Widdicombe, J. H. Mechanisms of Acid and Base Secretion by the Airway Epithelium. *The Journal of membrane biology* 211, 139-150, doi:10.1007/s00232-006-0861-0 (2006).
59. Fischer, H. Function of Proton Channels in Lung Epithelia. *Wiley Interdiscip Rev Membr Transp Signal* 1, 247-258, doi:10.1002/wmts.17 (2012).
60. Myerburg, M. M. et al. AMPK agonists ameliorate sodium and fluid transport and inflammation in cystic fibrosis airway epithelial cells. *Am J Respir Cell Mol Biol* 42, 676-684, doi:10.1165/2009-0147oc (2010).
61. Worthington, E. N. & Tarran, R. Methods for ASL measurements and mucus transport rates in cell cultures. *Methods Mol Biol* 742, 77-92, doi:10.1007/978-1-61779-120-8_5 (2011).
62. Schneider, C. A., Rasband, W. S. & Eliceiri, K. W. NIH Image to ImageJ: 25 years of image analysis. *Nature methods* 9, 671 (2012).

INCORPORATION BY REFERENCE

All patents and published patent applications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

We claim:

1. A method of treating cystic fibrosis, comprising conjointly administering to a patient in need thereof a therapeutically effective amount of (i) amphotericin B (AmB) or a pharmaceutically acceptable salt or hydrate thereof, and (ii) cholesterol or a pharmaceutically acceptable salt thereof, thereby treating the cystic fibrosis;
wherein the AmB and the cholesterol are administered in a molar ratio in the range from about 1:1 to about 1:2.5; the AmB and the cholesterol are administered in a single pharmaceutical composition; the AmB and the cholesterol are administered to an airway of the patient; the patient has two mutations in the CFTR anion channel; each copy of the CFTR gene contains one of the two mutations; and the two mutations are each independently selected from the following table:

| | | | |
|---|---|---|---|
| R75X | 663delT | 1525 – 1G –> A | 1924del7 |
| CFTRdele1 | G178R | 1525 – 2A –> G | 2055del9 –> A |
| M1V | 675del4 | S466X | 2105 – 2117del13ins-AGAAA |
| Q2X | E193X | L467P | 2118del4 |
| S4X | 711 + 1G –> T | 1548delG | 2143delT |
| 182delT | 711 + 3A –> G | S489X | G673X |

-continued

| | | | |
|---|---|---|---|
| CFTRdele2 | 711 + 5G -> A | S492F | 2183AA -> G or 2183del-AA -> G |
| CFTRdele2-4 | 712 - 1G -> T | 1609delCA | 2184insA |
| 185 + 1G -> T | H199Y | Q493X | 2184delA |
| CFTRdele2, 3 | P205S | W496X | 2185insC |
| W19X | L206W | I507del | Q685X |
| R75X | W216X | F508del | R709X |
| Q39X | Q220X | 1677delTA | K710X |
| A46D | L227R | V520F | Q715X |
| 296 + 1G -> A | 849delG | C524X | 2307insA |
| 296 + 1G -> T | 852del22 | Q525X | L732X |
| CFTRdele3-10, 14b-16 | CFTRdup6b-10 | CFTRdele11 | 2347delG |
| 297 - 1G -> A | 935delA | 1717 - 1G -> A | 2372del8 |
| E56K | Y275X | 1717 - 8G -> A | R764X |
| W57X | C276X | G542X | R785X |
| 306insA | 991del5 | S549R | R792X |
| 306delTAGA | 1078delT | S549N | 2556insAT |
| E60X | 1119delA | G550X | 2585delT |
| P67L | G330X | 1782delA | 2594delGT |
| R75X | R334W | G551S | E822X |
| 365-366insT | 1138insG | G551D | 2622 + 1G -> A |
| G85E | I336K | Q552X | E831X |
| 394delTT | T338I | R553X | W846X |
| L88X | S341P | A559T | Y849X |
| CFTRdele4-7 | 1154insTC | 1811 + 1634A -> G or 1811 + 1.6kbA -> G | R851X |
| CFTRdele4-11 | 1161delC | 1811 + 1G -> C | 2711delT |
| CFTR50kbdel | R347H | R560K | 2721del11 |
| 405 + 1G -> A | R347P | R560T | 2732insA |
| 405 + 3A -> C | R352Q | 1811 + 1G -> A | CFTRdele-14b-17b |
| 406 - 1G -> A | 1213delT | 1811 + 1643G -> T | W882X |
| E92K | 1248 + 1G -> A | 1812 - 1G -> A | 2789 + 5G -> A |
| E92X | 1249 - 1G -> A | R560S | 2790 - 1G -> C |
| Q98X | 1259insA | A561E | Q890X |
| 442delA | 1288insTA | V562I | S912X |
| 444delA | W401X | 1824delA | 2869insG |
| 457TAT -> G | 1341 + 1G -> A | 1833delT | Y913X |
| D110H | 1343delG | Y569D | 2896insAG |
| R117C | Q414X | E585X | L927P |
| R117H; 5T | D443Y | 1898 + 1G -> A | 2942insT |
| 541delC | 1461ins4 | 1898 + 1G -> C | 2957delT |
| 574delA | 1471delA | CFTRdele-13, 14a | S945L |
| 602del14 | A455E | 1898 + 3A -> G | 2991del32 |
| 621 + 1G -> T | 1497delGG | 1898 + 5G -> T | 3007delG |
| 3120G -> A | 3132delTG | H1054D | 3028delA |
| CFTRdele-17a, 17b | 3171delC | G1061R | G970R |
| CFTRdele-17a-18 | 3171insC | L1065P | CFTRdele-16-17b |
| 3120 + 1G -> A | Q1042X | R1066C | L1077P |
| 3121 - 1G -> A | 3271delGG | R1066H | W1089X |
| 3121 - 2A -> G | 3272-26A -> G | 3600G -> A | Y1092X |
| 3121 - 977_3499 + 248del2515 | 3600G -> A | CFTRdele19 | W1098X |
| 3349insT | CFTRdele19 | CFTRdele-19-21 | M1101K |
| 3659delC | CFTRdele19-21 | 3600 + 2insT | R1102X |
| 3667ins4 | 3600 + 2insT | 3600 + 5G -> A | E1104X |
| S1196X | 3600 + 5G -> A | R1158X | 3500 - 2A -> G |
| 3737delA | R1158X | R1162X | W1145X |
| W1204X | R1162X | W1282X | CFTRdele-22-24 |
| 3791delC | 3849G -> A | 4005 + 1G -> A | CFTRdele-22, 23 |
| Y122X | 3849 + 4A -> G | CFTR-dele21 | Q1330X |
| 3821delT | 3849 + 40A -> G | 4005 + 2T -> C | G1349D |
| I1234V | 3849 + 10kbC -> T | 4010del4 | 4209TGTT -> AA |
| 4326delTC | 3850 - 1G -> A | 4015delA | 4218insT |
| Q1411X | 3850 - 3T -> G | 4016insT | E1371X |
| Q1412X | G1244E | 4022insT | 4259del5 |
| 4374 + 1G -> T | 3876delA | 4021dupT | Q1382X |
| 4374 + 1G -> A | 3878delG | 4040delA | 4279insA |
| 4382delA | 31251N | N1303K | S1255P |
| 4428insGA | L1254X | Q1313X | S1255X |
| 3905insT | D259G. | | |

2. The method of claim 1, wherein the AmB and the cholesterol are administered in the form of a composition consisting essentially of water, AmB, and a liposomal membrane consisting of hydrogenated soy phosphatidylcholine, cholesterol, distearoylphosphatidylglycerol, alpha tocopherol, sucrose, and disodium succinate hexahydrate.

3. The method of claim 1, wherein the AmB and the cholesterol are administered as an aerosol.

4. The method of claim 1, wherein the two mutations are each independently selected from 2184delA, F508del, V520F, 1717-1G→A, E60X, G551D, R553X, and D259G.

5. The method of claim 4, wherein the patient has a pair of CFTR mutations selected from F508del/F508del, G551D/F508del, R553X/E60X, F508del/1717-1G→A, F508del/2184delA, and D259G/V520F.

6. The method of claim 4, wherein the patient has a pair of CFTR mutations selected from F508del/F508del, R553X/E60X, F508del/1717-1G→A, F508del/2184delA, and D259G/V520F.

7. The method of claim 6, wherein the cystic fibrosis is refractory to treatment with ivacaftor.

8. The method of claim 1, wherein one of the two mutations is Q2X or S4X.

9. The method of claim 1, wherein the two mutations are Q2X and S4X.

10. The method of claim 1, wherein the two mutations are F508del and F508del.

11. The method of claim 1, wherein the cystic fibrosis is refractory to treatment with ivacaftor.

12. The method of claim 3, wherein the cystic fibrosis is refractory to treatment with ivacaftor.

13. The method of claim 4, wherein the cystic fibrosis is refractory to treatment with ivacaftor.

14. The method of claim 5, wherein the cystic fibrosis is refractory to treatment with ivacaftor.

15. The method of claim 10, wherein the cystic fibrosis is refractory to treatment with ivacaftor.

16. The method of claim 3, wherein the two mutations are each independently selected from 2184delA, F508del, V520F, 1717-1G→A, E60X, G551D, R553X, and D259G.

17. The method of claim 3, wherein the patient has a pair of CFTR mutations selected from F508del/F508del, G551D/F508del, R553X/E60X, F508del/1717-1G→A, F508del/2184delA, and D259G/V520F.

18. The method of claim 3, wherein the patient has a pair of CFTR mutations selected from F508del/F508del, R553X/E60X, F508del/1717-1G→A, F508del/2184delA, and D259G/V520F.

19. The method of claim 3, wherein the two mutations are F508del and F508del.

20. The method of claim 19, wherein the cystic fibrosis is refractory to treatment with ivacaftor.

\* \* \* \* \*